(12) United States Patent
Huang

(10) Patent No.: US 8,691,972 B2
(45) Date of Patent: Apr. 8, 2014

(54) COMPOUNDS AND SYNTHESIS OF TELLURIUM-DERIVATIZED OLIGONUCLEOTIDES FOR STRUCTURAL AND FUNCTIONAL STUDIES

(76) Inventor: Zhen Huang, Marietta, GA (US)

( * ) Notice: Subject to any disclaimer, the term of this patent is extended or adjusted under 35 U.S.C. 154(b) by 0 days.

(21) Appl. No.: 13/553,901

(22) Filed: Jul. 20, 2012

(65) Prior Publication Data
US 2012/0282702 A1    Nov. 8, 2012

Related U.S. Application Data

(63) Continuation of application No. 13/322,392, filed as application No. PCT/US2010/036639 on May 28, 2010, now abandoned.

(60) Provisional application No. 61/182,580, filed on May 29, 2009.

(51) Int. Cl.
*C07H 19/00* (2006.01)

(52) U.S. Cl.
USPC ..... 536/28.54; 536/25.3; 536/23.2; 536/26.8; 536/28.2; 436/94

(58) Field of Classification Search
None
See application file for complete search history.

(56) References Cited

PUBLICATIONS

Puffer, B. et al. 2'-methylseleno-modified oligoribonucleotides for X-ray crystallography synthesized by the ACE RNA solid-phase approach, 2008, Nucleic Acids Research, vol. 36(3), pp. 970-983.*

\* cited by examiner

*Primary Examiner* — Robert Xu
(74) *Attorney, Agent, or Firm* — Arnall Golden Gregory LLP

(57) ABSTRACT

Disclosed are compounds of formula (I), a derivative, or a tautomer thereof, or a pharmaceutically acceptable salt of said compound or said tautomer. Also disclosed are methods of preparing compound of formula (I), a derivative, or a tautomer thereof, or a pharmaceutically acceptable salt of said compound or said tautomer. Further disclosed are methods of counducting drug discovery and research comprises applying the compound of formula (I), a derivative, or a tautomer thereof, or a pharmaceutically acceptable salt of said compound or said tautomer in an investigation.

17 Claims, 13 Drawing Sheets

1a: X=S: Methionine
1b: X=Se: Se-Met
1c: X=Te: Te-Met

2a: X=Se: 2'-Se-DNA or RNA
2b: X=Te: 2'-Te-DNA or RNA

SEQUENCE LISTING

```
<160> NUMBER OF SEQ ID NOS: 2

<210> SEQ ID NO 1
<211> LENGTH: 10
<212> TYPE: DNA
<213> ORGANISM: Unknown
<220> FEATURE:
<223> OTHER INFORMATION: mammal

<400> SEQUENCE: 1
ctcttgtccg                                                          10

<210> SEQ ID NO 2
<211> LENGTH: 11
<212> TYPE: DNA
<213> ORGANISM: Unknown
<220> FEATURE:
<223> OTHER INFORMATION: mammal

<400> SEQUENCE: 2
cggacaagaa g                                                        11
```

COMPOUNDS AND SYNTHESIS OF TELLURIUM-DERIVATIZED OLIGONUCLEOTIDES FOR STRUCTURAL AND FUNCTIONAL STUDIES

CROSS-REFERENCE TO RELATED APPLICATIONS

This application is a continuation and claims benefit of U.S. Non-Provisional application Ser. No. 13/322,392 filed Nov. 23, 2011, which is a U.S. National Stage Application under 35 U.S.C. §371 of International Application No. PCT/US2010/036639 filed May 28, 2010, which claims benefit of U.S. Provisional Application No. 61/182,580, filed May 29, 2009, the contents of which are all entirely incorporated herein by reference.

STATEMENT REGARDING FEDERALLY SPONSORED RESEARCH

This invention was made with government support under Grant Number MCB-0824837 awarded by the National Science Foundation. The U.S. government has certain rights in the invention. This invention was made with support of the Georgia Cancer Coalition and the Board of Regents of the University System of Georgia under that certain agreement in Atlanta, Ga. dated Oct. 1, 2002 and entitled "Agreement Re: Distinguished Cancer Clinicians and Scientists Program." The Board of Regents and the State of Georgia have certain rights in the invention.

REFERENCE TO SEQUENCE LISTING

The Sequence Listing created on Jul. 20, 2012 and submitted Jul. 20, 2012 as a text file named "SEQUENCE_LISTING.txt" in connection with U.S. Non-Provisional patent application Ser. No. 13/322,392, and having a size of 0.64 kilobytes is hereby incorporated by reference pursuant to 37 C.F.R. §1.52(e)(5).

BACKGROUND

Replacement of sulphur in methionine of protein with selenium has been widely used for protein structure determination by X-ray crystallography, where selenium serves as a scattering center for multi-wavelength anomalous dispersion (MAD) [W. A. Hendrickson, J. R. Horton, D. M. LeMaster, *EMBO. J.* 1990, 9, 1665-1672; W. A. Hendrickson, *Science* 1991, 254, 51-58; W. A. Hendrickson, *Trends. Biochem. Sci.,* 2001, 25, 637-643]. Recently selenium has been introduced into several different positions of DNAs and RNAs, including the 5' [N. Carrasco, D. Ginsburg, Q. Du, Z. Huang, *Nucleosides, Nucleotides, Nucleic Acids* 2001, 20, 1723-1734], 2' [Q. Du, N. Carrasco, M. Teplova, C. J. Wilds, M. Egli, Z. Huang, *J. Am. Chem. Soc.* 2002, 124, 24-25; N. Carrasco, Y. Buzin, E. Tyson, E. Halpert, Z. Huang, *Nucleic Acids Res.* 2004, 32, 1638-1646; J. Jiang, J. Sheng, N. Carrasco, Z. Huang, *Nucleic Acids Res.* 2007, 35, 477-485; J. Sheng, J. Jiang, J. Salon, Z. Huang, *Org. Lett.* 2007, 9, 749-752; C. Hobartner, R. Micura, *J. Am. Chem. Soc.* 2004, 126, 1141-1149; H. Moroder, C. Kreutz, K. Lang, A. Serganov, R. Micura, *J. Am. Chem. Soc.* 2006, 128, 9909-9918] and 4' [L. S. Jeong, D. K. Tosh, H. O. Kim, T. Wang, X. Hou, H. S. Yun, Y. Kwon, S. K. Lee, J. Choi, L. X. Zhao, *Org. Lett.* 2008, 10, 209-212; J. K. Watts, B. D. Johnston, K. Jayakanthan, A. S. Wahba, B. M. Pinto, M. J. Damha, *J. Am. Chem. Soc.* 2008, 130, 8578-8579] positions of the ribose, the phosphate backbone [C. J. Wilds, R. Pattanayek, C. Pan, Z. Wawrzak, M. Egli, *J. Am. Chem. Soc.* 2002, 124, 14910-14916; N. Carrasco, J. Caton-Williams, G. Brandt, S. Wang, Z. Huang, *Angew. Chem. Int. Ed. Engl.* 2006, 45, 94-97; G. Brandt, N. Carrasco, Z. Huang, *Biochemistry* 2006, 45, 8972-8977] and the nucleobases [J. Salon, J. Sheng, J. Jiang, G. Chen, J. Caton-Williams, Z. Huang, *J. Am. Chem. Soc.* 2007, 129, 4862-4863; J. Caton-Williams, Z. Huang, *Angew. Chem. Int. Ed. Engl.* 2008, 47, 1723-1725; J. Salon, J. Jiang, J. Sheng, O. O. Gerlits, Z. Huang, *Nucleic Acids Res.* 2008, 36, 7009-7018].

As a chalcogen element, tellurium follows sulfur and selenium in elemental group VI of the periodic table. Tellurium has a larger atomic radius (1.35 Å), compared with selenium (1.17 Å) and sulfur (1.04 Å), and has higher metallic property and stronger electron delocalizability. An electron-rich tellurium atom will likely donate electron and facilitate electron delocalization when it is introduced into DNA duplexes via nucleobases, which are relatively electron-deficient. Probably due to its metallic property and weak covalent bonds with carbon and hydrogen [L. Moroder, *J. Pept. Sci.* 2005, 11, 187-214], so far, no tellurium functionality has been discovered in any natural biological molecules. However, tellurium was successfully incorporated into proteins in 1989 through Te-resistant fungi grown in the presence of tellurite on a sulphur-free medium [S. E. Ramadan, A. A. Razak, A. M. Ragab, M. el-Meleigy, *Biol. Trace Elem. Res.* 1989, 20, 225-232]. Later, the Te-methionine derivatization for protein structure determination was investigated and developed. Boles and co-workers reported the expression of telluromethionine (TeMet) dihydrofolate reductase in 1994 [J. O. Boles, K. Lewinski, M. Kunkle, J. D. Odom, B. Dunlap, L. Lebioda, M. Hatada, *Nat. Struct. Biol.* 1994, 1, 283-284], and the Te-incorporation technique was further optimized to efficiently introduce TeMet into several proteins [N. Budisa, W. Karnbrock, S. Steinbacher, A. Humm, L. Prade, T. Neuefeind, L. Moroder, R. Huber, *J. Mol. Biol.* 1997, 270, 616-623]. Furthermore, the Te-protein stability under X-ray radiation and the isomorphism of the Te-proteins were confirmed, and more tellurium chemistry has also been developed [N. Budisa, B. Steipe, P. Demange, C. Eckerskorn, J. Kellermann, R. Huber, *Eur. J. Biochem.* 1995, 230, 788-796; M. Farina, F. A. Soares, G. Zeni, D. O. Souza, J. B. Rocha, *Toxicol. Lett.* 2004, 146, 227-235; W. Karnbrock, E. Weyher, N. Budisa, R. Huber, L. Moroder, *J. Am. Chem. Soc.* 1996, 118, 913-914].

The nucleobases play the most critical roles in duplex recognition of nucleic acids. Well-behaved base-pair recognition and sequence-dependent specificity of DNAs and RNAs have stimulated extensive research investigations, such as DNA nano-structure construction and self-assembling [a) J. Zheng, J. J. Birktoft, Y. Chen, T. Wang, R. Sha, P. E. Constantinou, S. L. Ginell, C. Mao, N. C. Seeman, *Nature* 2009, 461, 74-77. b) E. S. Andersen, M. Dong, M. M. Nielsen, K. Jahn, R. Subramani, W. Mamdouh, M. M. Goias, B. Sander, H. Stark, C. L. Oliveira, J. S. Pedersen, V. Birkedal, F. Besenbacher, K. V. Gothelf, J. Kjems, *Nature* 2009, 459, 73-76. c) P. W. Rothemund, *Nature* 2006, 440, 297-302. d) X. Xue, F. Wang, X. Liu, *J. Am. Chem. Soc.* 2008, 130, 3244-3245], disease and pathogen detection at single molecule level [A. Singer, M. Wanunu, W. Morrison, H. Kuhn, M. Frank-Kamenetskii, A. Meller, *Nano. Lett.* 2010, 10, 738-742], oligonucleotide drug discovery [K. Tiemann, J. J. Rossi, *EMBO Mol. Med.* 2009, 1, 142-151], and nanoelectronic device design based on DNA conductivity and charge migration [a) Y. C. Huang, D. Sen, *J. Am. Chem. Soc.* 2010, 132, 2663-2671. b) I. Kratochvilova, K. Kral, M. Buncek, A. Viskova, S. Nespurek, A. Kochalska, T. Todorciuc, M. Weiter, B. Schneider, *Biophys. Chem.* 2008, 138, 3-10. c) T. Ito, S. E. Rokita, *Angew. Chem. Int. Ed.* 2004, 43, 1839-1842. d) R. N. Barnett, C. L. Cleveland, A. Joy, U. Landman, G. B. Schuster, *Science* 2001, 294, 567-571. e) D. Porath, A. Bezryadin, S. de Vries, C. Dekker, *Nature* 2000, 403, 635-638. f) H. W. Fink, C. Schonenberger, *Nature* 1999, 398, 407-410]. Moreover, chemical modifications of nucleobases have been widely used to selectively tailor the biochemical and biophysical properties of DNAs and RNAs and to probe their biochemical and biological mechanisms, including base-pairing specificity, polymerase recognition, and DNA damaging and repairing [a) Z. Yang, F. Chen, S. G. Chamberlin, S. A. Benner, *Angew. Chem. Int. Ed.* 2010, 49, 177-180. b) M. Egli, P. S. Pallan, *Chem. Biodivers.* 2010, 7, 60-89. c) A. E. Hassan, J. Sheng, W. Zhang, Z. Huang, *J. Am. Chem. Soc.* 2010, 132, 2120-2121. d) J. C. Delaney, J. Gao, H. Liu, N. Shrivastav, J. M. Essigmann, E. T. Kool, *Angew. Chem. Int. Ed. Engl.* 2009, 48, 4524-4527. e) M. Ljungman, *Chem. Rev.* 2009, 109, 2929-2950. f) A. M. Sismour, S. A. Benner, *Nucleic Acids Res.* 2005, 33, 5640-5646. g) T. W. Kim, J. C. Delaney, J. M. Essigmann, E. T. Kool, *Proc. Natl. Acad. Sci. USA* 2005, 102, 15803-15808]. Furthermore, the conductivity of DNAs has been studied extensively via nucleobase modification, metallization and conjugating with conductive nanoparticles or polymers through scanning tunneling microscopy (STM) imaging [I. Kratochvilova, K. Kral, M. Buncek, A. Viskova, S. Nespurek, A. Kochalska, T. Todorciue, M. Weiter, B. Schneider, *Biophys. Chem.* 2008, 138, 3-10; a) E. Braun, Y. Eichen, U. Sivan, G. Ben-Yoseph, Nature 1998, 391, 775-778. b) J. L. Coffer, S. R. Bigham, X. Li, R. F. Pinizzotto, Y. G. Rho, R. M. Pirtle, I. L. Pirtle, *Appl. Phys. Lett.* 1996, 69, 3851-3853. c) Y. F. Ma, J. M. Zhang, G. J. Zhang, H. X. He, *J. Am. Chem. Soc.* 2004, 126, 7097-7101. d) X. Guo, A. A. Gorodetsky, J. Hone, J. K. Barton, C. Nuckolls, *Nat. Nanotechnol.* 2008, 3, 163-167. e) B. Elias, F. Shao, J. K. Barton, *J. Am. Chem. Soc.* 2008, 130, 1152-1153].

Therefore, there is a need existing for the identification of new Te-nucleoside phosphoramidites and Te-modified oligonucleotides, and their derivatives in DNAs, RNAs and modified nucleic acids.

SUMMARY

Disclosed are compound of formula (I), or a tautomer thereof, or a pharmaceutically acceptable salt of said compound or said tautomer:

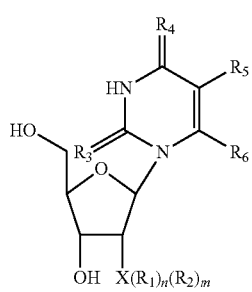

(I)

wherein:
X is selenium or tellurium;
$R_1$ is linear or branched alkyl, or aryl;
$R_2$ is selected from the group consisting of hydrogen, halogen, alkyl, aryl, hydroxyl, thiol, amino, alkyloxyl, aryloxyl, acyloxyl, alkylthiol, arylthiol, alkylseleno, arylseleno, alkyltelluro, aryltelluro, alkylamino, arylamino and acylamino;

$R_3$ and $R_4$ are each independently selected from the group consisting of oxygen, sulfur, selenium, tellurium, amino, alkylamino, arylamino and acylamino;

$R_5$ and $R_6$ are each independently selected from the group consisting of hydrogen, halogen, alkyl, aryl, hydroxyl, thiol, amino, alkyloxyl, aryloxyl, acyloxyl, alkylthiol, arylthiol, alkylamino, arylamino and acylamino; and n and m are a subscript selected from 0 to 20.

Also disclosed are methods of preparing compound of formula (I), or a tautomer thereof, or a pharmaceutically acceptable salt of said compound or said tautomer. Further disclosed are method of counducting drug discovery and research comprises applying the compound of formula (I), or a tautomer thereof, or a pharmaceutically acceptable salt of said compound or said tautomer in an investigation.

BRIEF DESCRIPTION OF THE DRAWINGS

The accompanying drawings, which are incorporated in and constitute a part of this specification, illustrate several forms and together with the description illustrate the disclosed compounds and methods.

DETAILED DESCRIPTION

Figure 1:
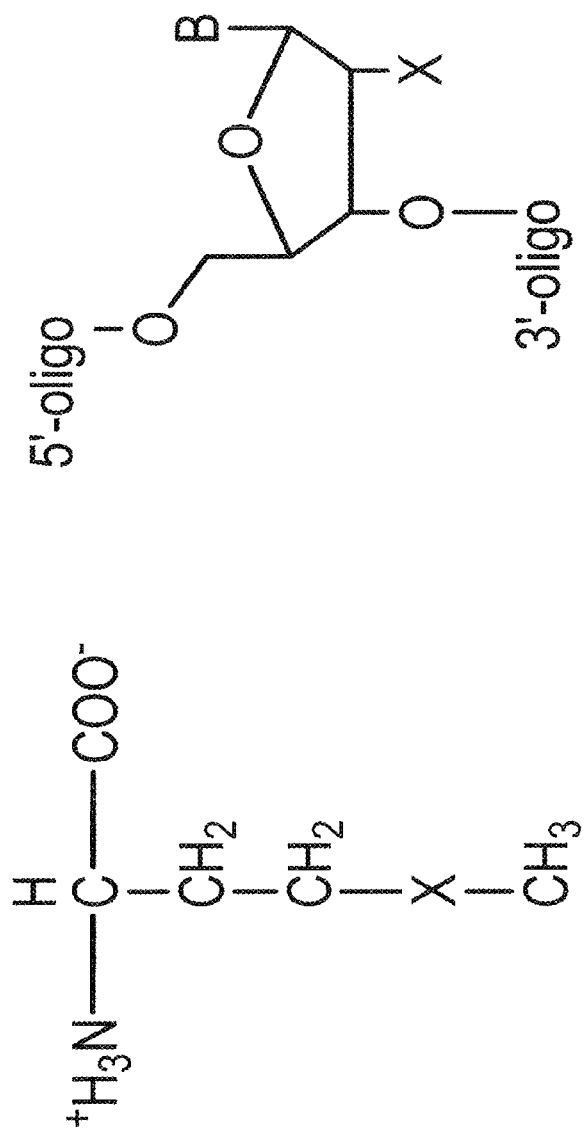
FIG. 1. A representation of the structures of certain selenium- and tellurium-derivatized methionine and oligonucleotide according to some forms of the disclosure.

Before the present compounds, compositions, articles, devices, and/or methods are disclosed and described, it is to be understood that they are not limited to specific synthetic methods or specific treatment methods unless otherwise specified, or to particular reagents unless otherwise specified, as such may, of course, vary. It is also to be understood that the terminology used herein is for the purpose of describing particular forms only and is not intended to be limiting.

Disclosed are methods of synthesis of unique Te-nucleoside phosphoramidites and Te-modified oligonucleotides. The method includes protected the 2'-tellurium functionality by alkylation. As a result, the Te-functionality is compatible with the solid-phase synthesis and the unique Te-oligonucleotides are stable during the deprotection and purification. In addition, the redox properties of the Te-functionalities have been explored. It is found that the telluride and telluroxide DNAs are interchangeable by redox reactions. The synthesized Te-derivatization of nucleic acids provides a novel approach for investigation of the DNA damages as well as for structure and function studies of nucleic acids and their protein complexes.

The electronic and atomic properties of tellurium are ideal to generate clear isomorphous signals using just the normal in-house X-ray diffraction facility (Cu, Kα wavelength: 1.54 Å). It is demonstrated that a synchrotron facility is not necessary to collect X-ray diffraction data for phase and structure determination of protein derivatized with the Te-functionality. This Te-derivatization strategy is a promising alternative to the conventional multiple isomorphous replacements (MIR) [C. W. Nogueira, G. Zeni, J. B. Rocha, Chem. Rev. 2004, 104, 6255-6285.] by the soaking procedures. It is found that under elevated temperature, the Te-DNA can also be site-specifically fragmented oxidatively or reductively when the 2'-Te-Ph functionality is present, while the elimination of the nucleobase is observed in the presence of the 2'-Te-Me functionality. Moreover, the stability of the DNA duplexes derivatized with the Te-functionalities has been investigated.

Materials

A. Compounds

Disclosed are compounds of formula (I), or a tautomer thereof, or a pharmaceutically acceptable salt of said compound or said tautomer;

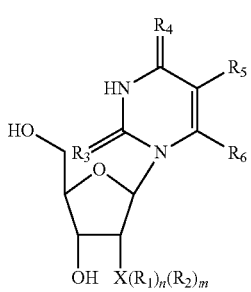

(I)

wherein:
X is selenium or tellurium;
$R_1$ is linear or branched alkyl, or aryl;
$R_2$ is selected from the group consisting of hydrogen, halogen, alkyl, aryl, hydroxyl, thiol, amino, alkyloxyl, aryloxyl, acyloxyl, alkylthiol, arylthiol, alkylseleno, arylseleno, alkyltelluro, aryltelluro, alkylamino, arylamino and acylamino;
$R_3$ and $R_4$ are each independently selected from the group consisting of oxygen, sulfur, selenium, tellurium, amino, alkylamino, arylamino and acylamino;
$R_5$ and $R_6$ are each independently selected from the group consisting of hydrogen, halogen, alkyl, aryl, hydroxyl, thiol, amino, alkyloxyl, aryloxyl, acyloxyl, alkylthiol, arylthiol, alkylamino, arylamino and acylamino; and
n and m are a subscript selected from 0 to 20.

In some forms, the compound of formula (I) can tautomerize to form a tautomer of the compound of formula (I) where said tautomer has a formula (II):

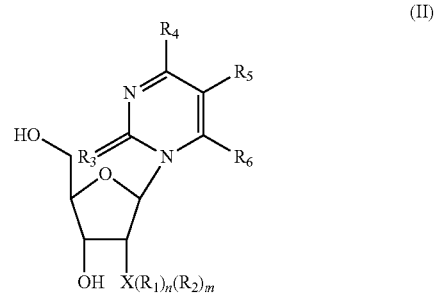

(II)

wherein R4 is selected from the group consisting of hydrogen, halogen, alkyl, aryl, hydroxyl, thiol, alkylthiol, arylthiol, amino, alkylamino, arylamino and acylamino.

In some forms, the compound of formula (I) can be a compound wherein the unsaturated six-member base ring of the nucleobase is cytosine, thymine or uracil. In some other forms, the compound of formula (I) can be a compound wherein X is tellurium; and $R_1$ is linear or branched alkyl, or aryl.

In some forms, the compound of formula (I) can be a compound wherein $R_5$ is hydrogen or alkyl. In some other forms, a derivative of the compound of formula (I) can be a compound of formula (III):

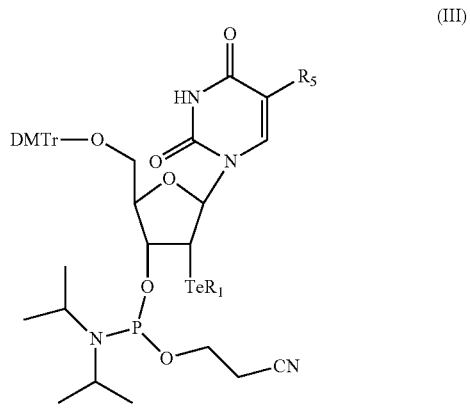

(III)

wherein DMTr represents dimethoxytrityl.

In some forms, the derivative of the compound of formula (I) can be a compound wherein the $R_1$ is methyl or phenyl. In some other forms, the derivative of the compound of formula (I) can be a compound wherein the $R_5$ is hydrogen or methyl.

In some other forms, the derivative of the compound of formula (I) can be a compound of formula (IV):

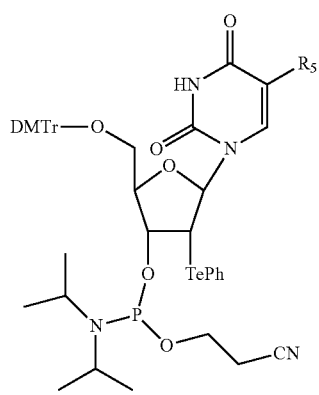

(IV)

wherein $R_5$ is hydrogen or methyl. In some other forms, the derivative of the compound of formula (I) can be a compound of formula (V):

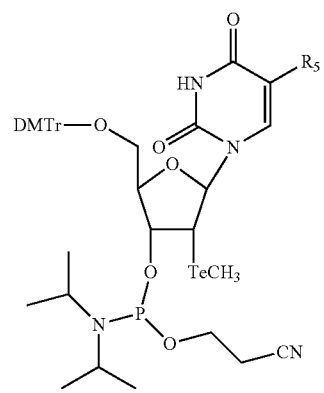

(V)

wherein $R_5$ is hydrogen or methyl.

In some forms, the derivative of the compound of formula (I) can be a compound wherein the derivative is an telluride (Te)-oligonucleotide, telluride(Te)-DNA, or telluride(Te)-RNA. In some other forms, the derivative of the compound of formula (I) can be a compound of formula (VI):

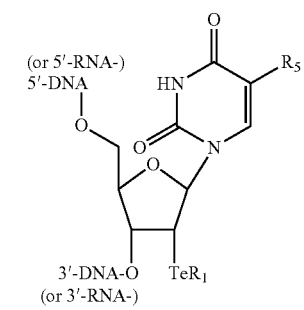

(VI)

wherein $R_1$ is methyl or phenyl; and $R_5$ is hydrogen or methyl.

In some forms, the derivative of the compound of formula (I) can be a compound wherein the telluride DNA (or RNA) is oxidized to form a telluroxide DNA (or RNA) and/or tellurone DNA (or RNA) which has a structure of formula VIIa or VIIb respectively:

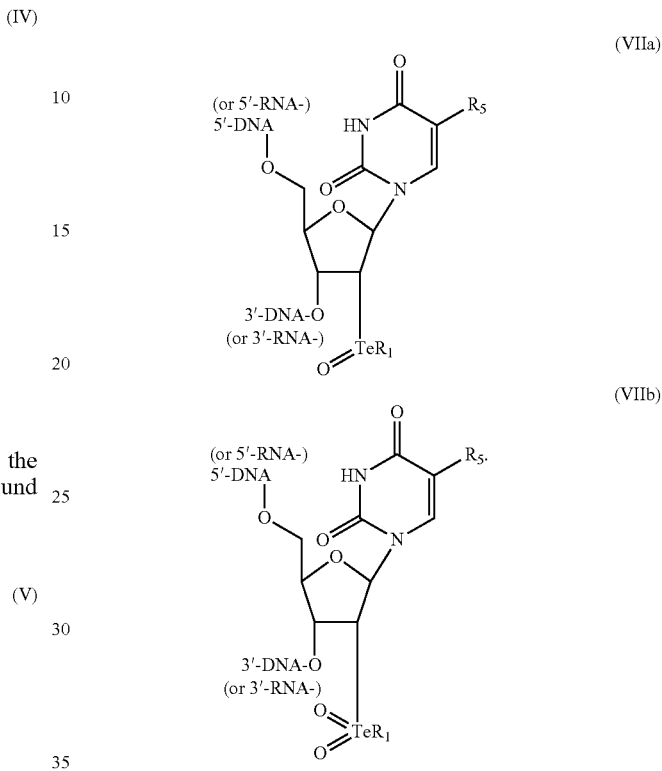

In some forms, the derivative of the compound of formula (I) can be a compound wherein the derivative is used as a building block to construct the corresponding telluride(Te)-oligonucleotide, telluride(Te)-DNA, or telluride(Te)-RNA.

1. Isomers

When an asymmetric center is present in a compound of formula I or a derivative of the compound of formula I, hereinafter referred to as the disclosed compounds, the compound may exist in the form of optical isomers (enantiomers). In some forms, the disclosed compounds and compositions can comprise enantiomers and mixtures, including racemic mixtures of the compounds of formula I. In some forms, for compounds of formula I that contain more than one asymmetric center, the disclosed compounds and compostions can comprise diastereomeric forms (individual diastereomers and mixtures thereof) of compounds. When a compound of formula I contains an alkenyl group or moiety, geometric isomers may arise.

2. Tautomeric Forms

The disclosed compounds comprise the tautomeric forms of compounds of formula I. Where structural isomers are interconvertible via a low energy barrier, tautomeric isomerism ('tautomerism') can occur. This can take the form of proton tautomerism in compounds of formula I containing, for example, an imino, keto, or oxime group, or so-called valence tautomerism in compounds which contain an aromatic moiety. It follows that a single compound may exhibit more than one type of isomerism. The various ratios of the tautomers in solid and liquid form are dependent on the various substituents on the molecule as well as the particular crystallization technique used to isolate a compound.

3. Salts

The disclosed compounds can be used in the form of salts derived from inorganic or organic acids. Depending on the particular compound, a salt of the compound can be advantageous due to one or more of the salt's physical properties, such as enhanced pharmaceutical stability in differing temperatures and humidities, or a desirable solubility in water or oil. In some instances, a salt of a compound can also be used as an aid in the isolation, purification, and/or resolution of the compound.

Where a salt is intended to be administered to a patient (as opposed to, for example, being used in an in vitro context), the salt preferably is pharmaceutically acceptable. The term "pharmaceutically acceptable salt" refers to a salt prepared by combining a compound, such as the disclosed compounds, with an acid whose anion, or a base whose cation, is generally considered suitable for human consumption. Pharmaceutically acceptable salts are particularly useful as products of the disclosed methods because of their greater aqueous solubility relative to the parent compound. For use in medicine, the salts of the disclosed compounds are non-toxic "pharmaceutically acceptable salts." Salts encompassed within the term "pharmaceutically acceptable salts" refer to non-toxic salts of the disclosed compounds which are generally prepared by reacting the free base with a suitable organic or inorganic acid.

Suitable pharmaceutically acceptable acid addition salts of the disclosed compounds, when possible include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include, for example, aliphatic, cycloaliphatic, aromatic, araliphatic, heterocyclylic, carboxylic, and sulfonic classes of organic acids.

Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, algenic acid, β-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, tosylate, and undecanoate.

Furthermore, where the disclosed compounds carry an acidic moiety, suitable pharmaceutically acceptable salts thereof can include alkali metal salts, e.g., sodium or potassium salts; alkaline earth metal salts, e.g., calcium or magnesium salts; and salts formed with suitable organic ligands, e.g., quaternary ammonium salts. In some forms, base salts are formed from bases which form non-toxic salts, including aluminum, arginine, benzathine, choline, diethylamine, diolamine, glycine, lysine, meglumine, olamine, tromethamine and zinc salts.

Organic salts can be made from secondary, tertiary or quaternary amine salts, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups can be quaternized with agents such as lower alkyl (C1-C6) halides (e.g., methyl, ethyl, propyl, and butyl chlorides, bromides, and iodides), dialkyl sulfates (e.g., dimethyl, diethyl, dibuytl, and diamyl sulfates), long chain halides (e.g., decyl, lauryl, myristyl, and stearyl chlorides, bromides, and iodides), arylalkyl halides (e.g., benzyl and phenethyl bromides), and others. In some forms, hemisalts of acids and bases can also be formed, for example, hemisulphate and hemicalcium salts. The disclosed compounds can exist in both unsolvated and solvated forms. A "solvate" as used herein is a nonaqueous solution or dispersoid in which there is a noncovalent or easily dispersible combination between solvent and solute, or dispersion means and disperse phase.

4. Prodrugs

Also disclosed are so-called "prodrugs" of the disclosed compounds. Thus, certain derivatives of the disclosed compounds which have little or no pharmacological activity themselves can, when administered into or onto the body, be converted into the disclosed compounds having the desired activity, for example, by hydrolytic cleavage. Such derivatives are referred to as "prodrugs." Further information on the use of prodrugs can be found in "Prodrugs as Novel Delivery Systems, Vol. 14, ACS Symposium Series (T Higuchi and W Stella) and "Bioreversible Carriers in Drug Design," Pergamon Press, 1987 (ed. E B Roche, American Pharmaceutical Association). Prodrugs as disclosed herein can, for example, be produced by replacing appropriate functionalities present in the compounds of formula I with certain moieties known to those skilled in the art as "pro-moieties" as described, for example, in "Design of Prodrugs" by H Bundgaard (Elsevier, 1985).

5. Isotopes

Also disclosed are isotopically labelled compounds, which are identical to those compounds recited in formula I, but for the fact that one or more atoms are replaced by an atom having an atomic mass or mass number different from the atomic mass or mass number usually found in nature. Examples of isotopes that can be incorporated into disclosed compounds include isotopes of hydrogen, carbon, nitrogen, oxygen, phosphorous, sulfur, fluorine and chlorine, such as $^2H$, $^3H$, $^{13}C$, $^{11}C$, $^{14}C$, $^{15}N$, $^{18}O$, $^{17}O$, $^{31}P$, $^{32}P$, $^{35}S$, $^{18}F$, and $^{36}Cl$, respectively. Disclosed compounds, prodrugs thereof, and pharmaceutically acceptable salts of said compounds or of said prodrugs which contain the aforementioned isotopes and/or other isotopes of other atoms are contemplated. Certain isotopically labelled disclosed compounds, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of formula I (and other disclosed compounds) and prodrugs thereof can generally be prepared by carrying out the procedures disclosed in the Schemes and/or in the Examples and Preparations below, by substituting a readily available isotopically labelled reagent for a non-isotopically labelled reagent.

6. General Synthetic Schemes

The compounds of the formula I (and other disclosed compounds), or the derivatives of the compounds of formula I, or the pharmaceutically acceptable salts of the compounds and derivatives of the compounds of formula I, can be prepared by the methods as illustrated by general reaction schemes shown below, by examples described in the "Examples" section, together with synthetic methods known in the art of organic chemistry, or modifications and derivatisations that are familiar to those of ordinary skill in the art. The starting materials used herein are commercially available or can be prepared by routine methods known in the art (such as those methods disclosed in standard reference books such as the COMPENDIUM OF ORGANIC SYNTHETIC METHODS, Vol. I-VI (published by Wiley-Interscience)). Preferred methods include, but are not limited to, those described below. During any of the following synthetic sequences it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991, and T. W. Greene and P. G. M. Wuts, Protective Groups in Organic Chemistry, John Wiley & Sons, 1999, which are hereby incorporated by reference. Isolation and purification of the products is accomplished by standard procedures, which are known to a chemist of ordinary skill.

A general reaction scheme for the preparation of the compound of formula I or the derivative of such compound is illustrated in scheme 1:

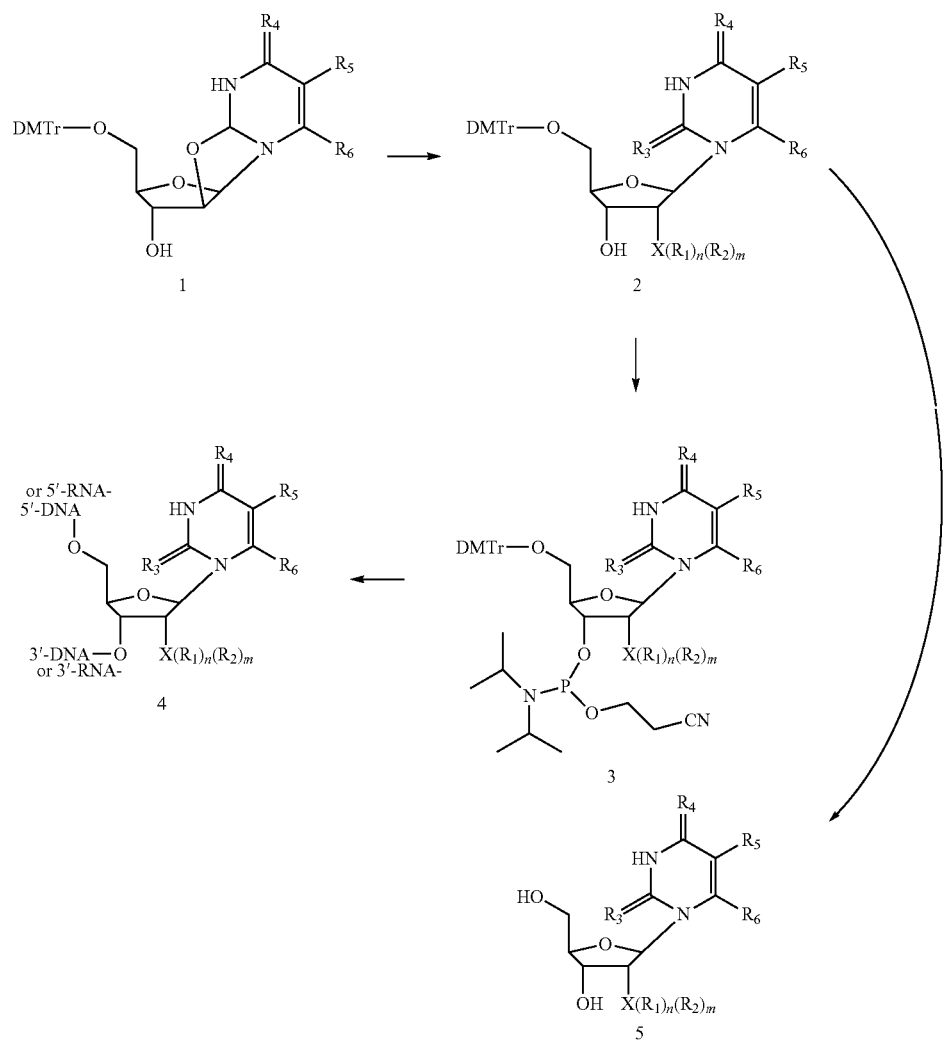

where compound 1 is treated with a suitable selenium or tellurium reagent under a suitable temperature via $SN_2$ reaction to provide compound 2; compound 2 is converted to compound 3 via phosphitylation; and compound 3 is converted to compound 4 via solid phase synthesis; alternatively, compound 2 is deprotected to provide compound 5.

Another general reaction scheme for the preparation of the compound of formula I or the derivative of such compound is illustrated in scheme 2:

Scheme 2

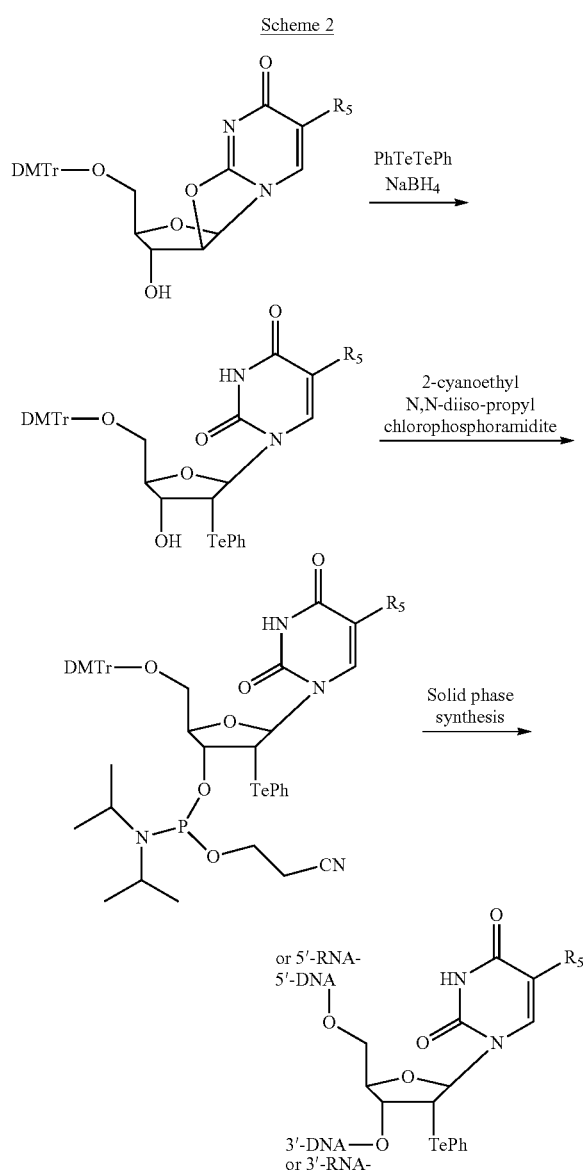

in which the starting material is treated with diphenylditelluride and NaBH$_4$ to provide 2'-Te-nucleoside; the 2'-Te-nucleoside is converted to the corresponding phosphoramidity derivative via phosphitylation; and the phosphoramidity derivative is converted to 2'-Te-DNAs (or RNAs) via solid phase synthesis. In some forms, the preparation of the compound of formula I or the derivative of such compound is according to scheme 2 can be a preparation wherein R$_5$ is hydrogen or methyl.

Figure 8:
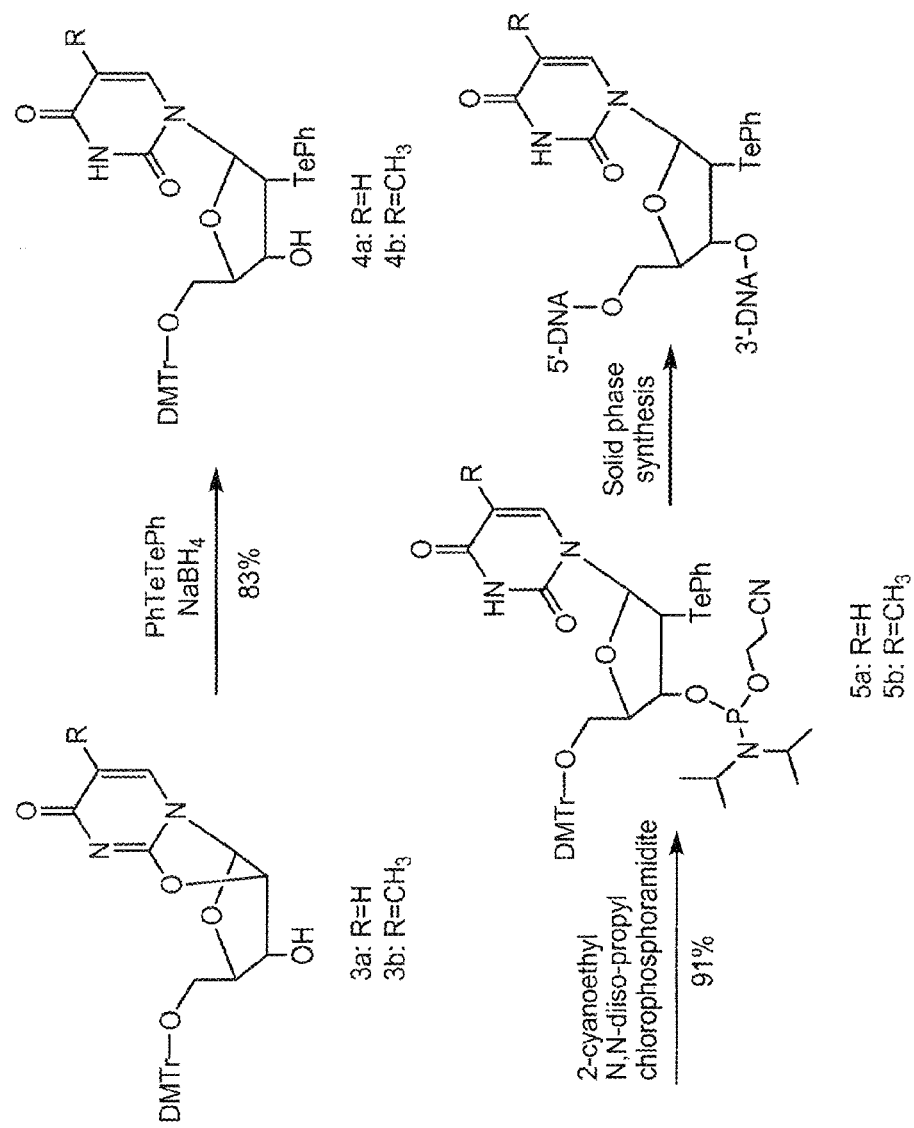
FIG. 8. A representation of the method of synthesis of 2'-Te-uridine and 2'-Te-thymidine phosphoramidites (5a and 5b) and the associated Te-DNAs according to some forms of the disclosure.
Figure 9:
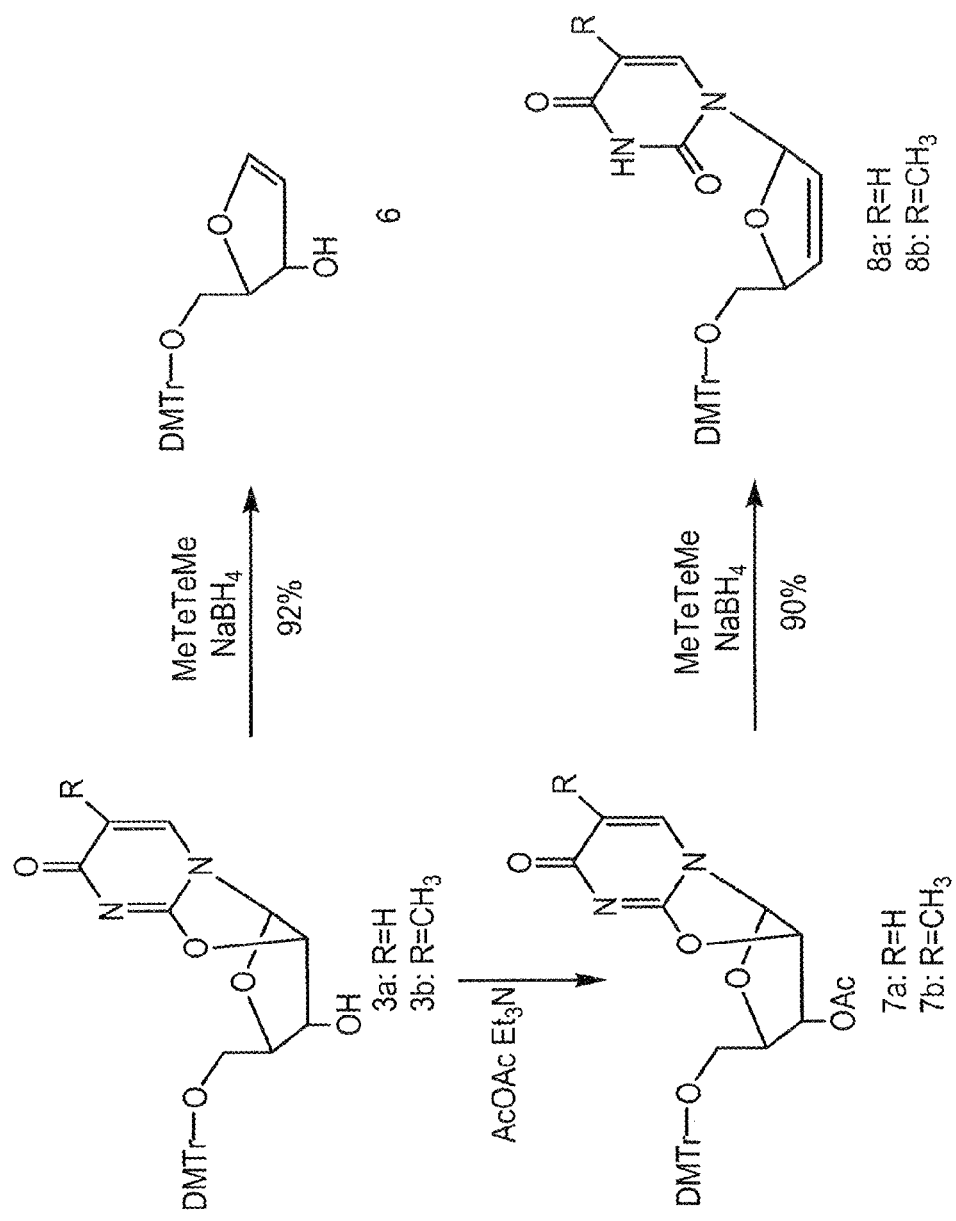
FIG. 9. A representation of the method of synthesis of certain compounds via elimination reactions resulting from the 2'-Te-Me functionality according to some forms of the disclosure.

FIG. 8 presents a method for synthesizing 2'-Te-nucleoside phosphoramidites (5a and 5b) and the associated 2'-Te-DNAs according to a form of the disclosure. In FIG. 8, the 5'-DMTr-2,2'-anhydrouridine 3a and thymidine 3b were the starting materials, and methods for synthesizing those starting materials are known in the art [N. Carrasco, Y. Buzin, E. Tyson, E. Halpert, Z. Huang, *Nucleic Acids Res.* 2004, 32, 1638-1646; J. Sheng, J. Jiang, J. Salon, Z. Huang, *Org. Lett.* 2007, 9, 749-752]. The tellurium functionalities were introduced by a SN$_2$ reaction, where the commercially available tellurium reagents (dimethylditelluride and diphenylditelluride) were reduced first. As shown in FIG. 8, the Te-incorporation was achieved with diphenylditelluride. It turned out that it is easy to reduce diphenylditelluride with sodium borohydride in dry THF at room temperature. The ring opening reaction underwent well at 50° C., allowing the phenyl telluride nucleophile to attack the 2'-position from the α face and yielding a satisfied yield. The generated key intermediates 4a and 4b were successfully converted to the corresponding phosphoramidites 5a and 5b in high yields by following the standard protocol [N. Carrasco, Y. Buzin, E. Tyson, E. Halpert, Z. Huang, *Nucleic Acids Res.* 2004, 32, 1638-1646.]. On contrary, it is difficult to reduce dimethylditelluride efficiently with sodium borohydride even at an elevated temperature, probably due to the relatively higher reactivity of methyl telluride. As shown in FIG. 9, at the elevated temperature for the Te-functionization, the debased compound (6) was observed as the major product because of the 1',2' elimination. When the 3'-hydroxyl group of 3a and 3b was protected through acetylation to prevent its deprotonation during the Te-functionization, the 2',3' elimination was observed [J. Sheng, A. E. Hassan, Z. Huang, *J. Org. Chem.* 2008, 73, 3725-3729], which generates the olefin analogs (8a and 8b), precursors of the anti-viral drug d4T.

Another general reaction scheme for the preparation of the compound of formula I or the derivative of such compound is illustrated in scheme 3:

Scheme 3

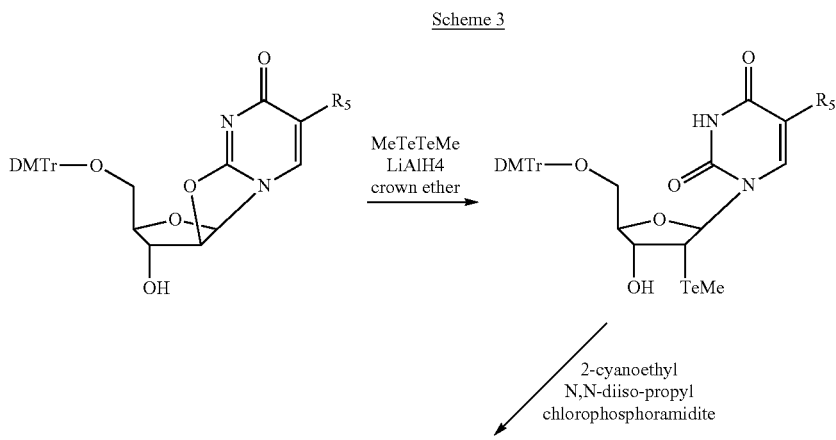

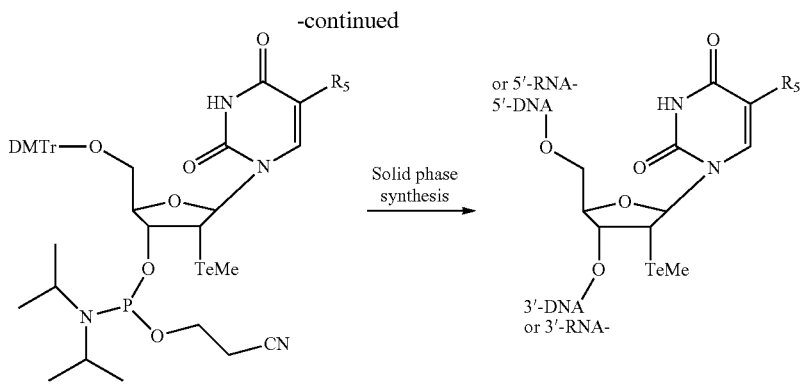

in which the starting material is treated with dimethylditelluride, LiAlH$_4$ and crown ether to provide 2'-Te-nucleoside; the 2'-Te-nucleoside is converted to the corresponding phosphoramidity derivative via phosphitylation; and the phosphoramidity derivative is converted to 2'-Te-DNAs (or RNAs) via solid phase synthesis. In some forms, the preparation of the compound of formula I or the derivative of such compound is according to scheme 3 can be a preparation wherein R$_5$ is hydrogen or methyl.

Figure 10:
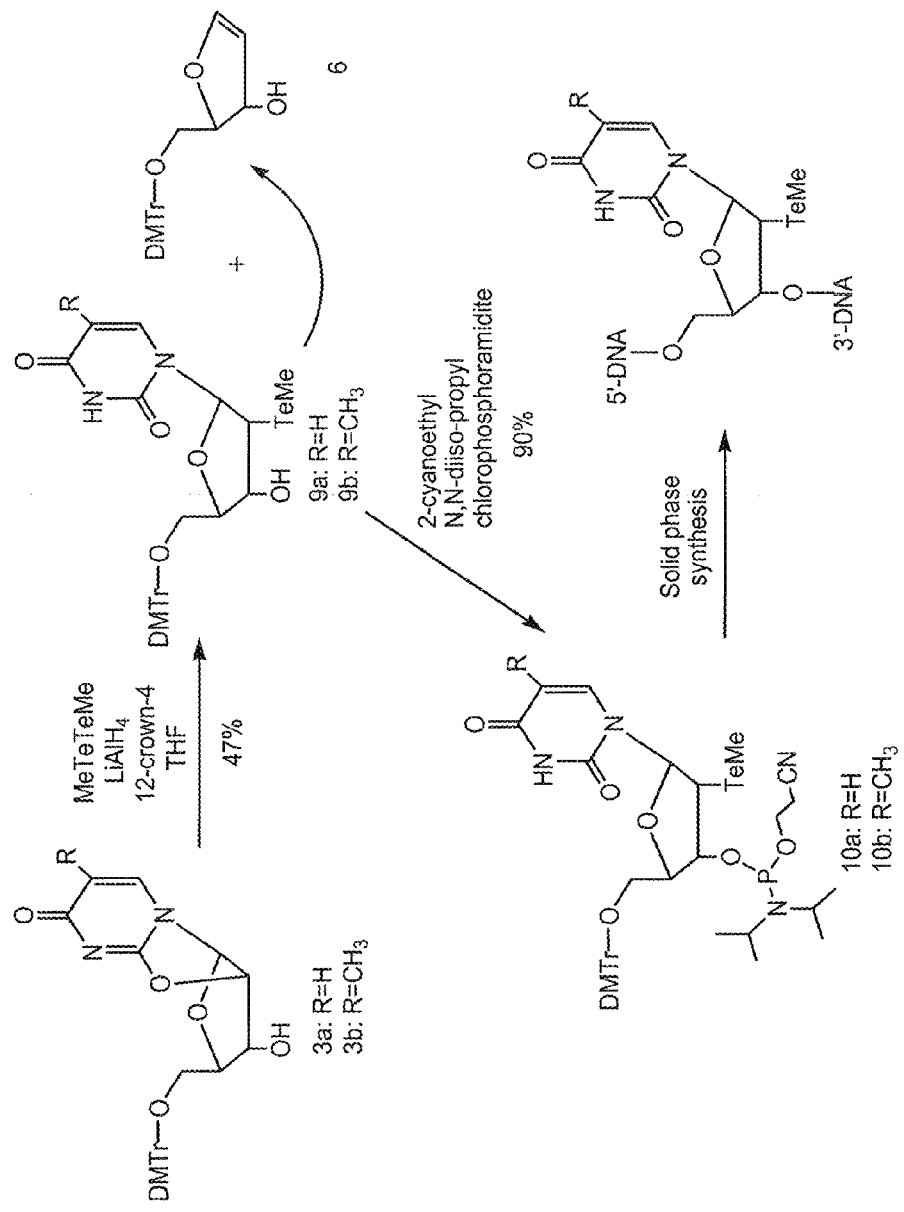
FIG. 10. A representation of the method of synthesis of 2'-Te-uridine and 2'-Te-thymidine phosphoramidites (10a and 10b) and the associated Te-DNAs according to some forms of the disclosure.

As shown in FIG. 10, in one experiment due to the difficulty of the efficient dimethylditelluride reduction, a stronger reducing reagent (such as LiAlH$_4$) was used. However, only trace amount of the desired compound (9) was observed. In order to minimize by-product formation, the telluride incorporation was conducted at a lower temperature (e.g., 0° C.). Furthermore, crown ether (e.g., 12-crown-4) was used to chelate lithium ions in order to enhance the methyltelluride reactivity. The desired product was obtained in 47% yield, while the 1',2'-eliminated product was still formed as the major by-product. The characteristic chemical shift of the Te-methyl group was observed at −21.2 ppm in $^{13}$C-NMR spectrum. Moreover, the tellurium isotope distributions in the HR-MS spectra indicated the incorporation of the Te-functionality. The generated key intermediates 9a and 9b were successfully converted to the corresponding phosphoramidites 10a and 10b in high yields by following the standard protocol [N. Carrasco, Y. Buzin, E. Tyson, E. Halpert, Z. Huang, *Nucleic Acids Res.* 2004, 32, 1638-1646].

These synthesized Te-phosphoramidites were incorporated into oligonucleotides by solid-phase synthesis generally in over 95% coupling yield, using 5-(benzylmercapto)-1H-tetrazole (5-BMT) as the activator. It was found that the bulky 2'-Te-moieties didn't significantly affect the coupling reaction, and these 2'-Te-modified phosphoramidites could achieve almost quantitative coupling even with a standard 25 seconds of coupling time. The Te-oligonucleotides were synthesized via the DMTr-on mode using ultra-mild phosphoramidites and cleaved with K$_2$CO$_3$ at room temperature for 8 hours [J. Salon, J. Sheng, J. Jiang, G. Chen, J. Caton-Williams, Z. Huang, *J. Am. Chem. Soc.* 2007, 129, 4862-4863]. To reduce the partially oxidized Te-DNAs, a diborane treatment was performed right after the deprotection step. As an example, the HPLC analysis profile of a crude 2'-TePh-T DNA with DMTr-on is shown in FIG. 2.

Figure 2:
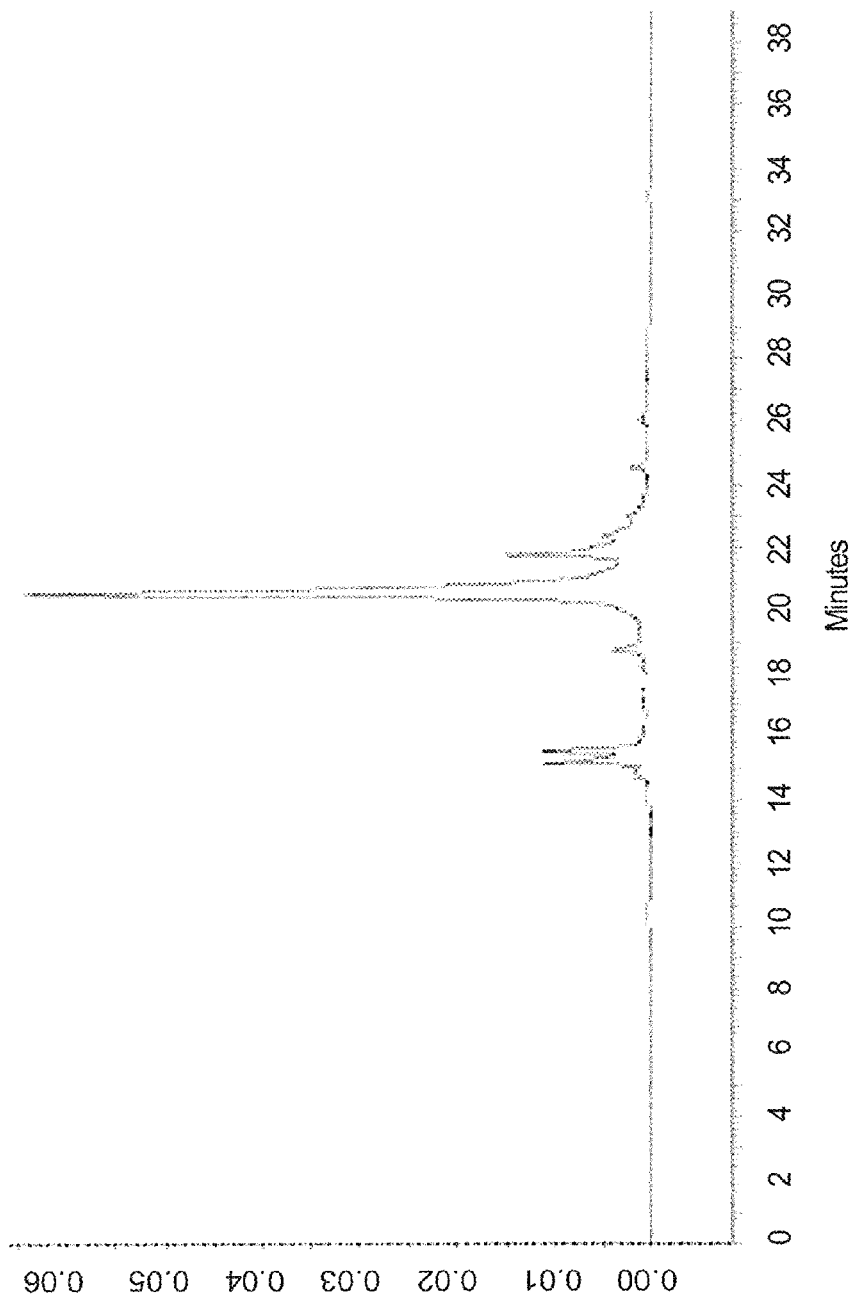
FIG. 2. A representation of the HPLC analysis of the Te-DNA: 5'-DMTr-G(2'-TePh-dU)GTACAC-3' according to some forms of the disclosure.

FIG. 2 shows the HPLC analysis of the Te-DNA: 5'-DMTr-G(2'-TePh-dU)GTACAC-3'. This analysis was performed on a Zorbax SB-C18 column (4.6×250 mm) with a linear gradient from buffer A (20 mM TEAAc: triethylammonium acetate, pH 7.1) to 100% buffer B (50% acetonitrile in 20 mM TEAAc) in 20 minutes. The retention time of the full-length Te-DNA is 20.7 minutes.

In addition, Te-coupling yield was determined as over 95%. After the HPLC purification with DMTr-on, the DMTr group was removed by treatment with 3% trichloroacetic acid, and the oligonucleotides were purified again by HPLC, followed by MALDI-TOF MS analysis to confirm the integrity of these Te-DNAs (Table 1 and FIG. 3). It was found that both methyltelluride and phenyltelluride functionalities are stable during the deprotection and purification.

TABLE 1

MALDI-TOF analysis of 2'-Te modified oligonucleotides

| DNA sequences | Formula | MS [M − H$^+$]$^-$ (Calcd.) |
|---|---|---|
| G(2'-TeMe-dU)GTACAC | C$_{78}$H$_{99}$N$_{30}$O$_{46}$P$_7$Te | 2536.1 (2536.2) |
| ATGG(2'-TeMe-dU)GCTC | C$_{88}$H$_{112}$N$_{32}$O$_{54}$P$_8$Te | 2856.3 (2856.4) |
| G(2'-TePh-dU)GTACAC | C$_{83}$H$_{101}$N$_{30}$O$_{46}$P$_7$Te | 2599.4 (2599.3) |
| ATGG(2'-TePh-dU)GCTC | C$_{93}$H$_{114}$N$_{32}$O$_{54}$P$_8$Te | 2919.0 (2918.5) |
| GCG(2'-TePh-dU)ATACGC | C$_{102}$H$_{125}$N$_{38}$O$_{58}$P$_9$Te | 3218.0 (3216.7) |
| G(2'-TePh-dU)GTACAC | C$_{84}$H$_{103}$N$_{30}$O$_{46}$P$_7$Te | 2611.8 (2612.3) |
| ATGG(2'-TePh-dU)GCTC | C$_{94}$H$_{116}$N$_{32}$O$_{54}$P$_8$Te | 2933.3 (2932.5) |
| CT(2'-TePh-dU)CTTGTCCG | C$_{111}$H$_{140}$N$_{32}$O$_{69}$P$_{10}$Te | 3464.5 (3465.4) |
| CT(2'-TeMe-dU)CTTGTCCG | C$_{106}$H$_{138}$N$_{32}$O$_{69}$P$_{10}$Te | 3400.5 (3401.8) |

Another general reaction scheme for the preparation of the compound of formula I or the derivative of such compound is a preparation wherein the transformation between 2'-telluride DNA (or RNA) and 2'-telluroxide (or tellurone) DNA (or RNA) is illustrated in scheme 4:

Scheme 4

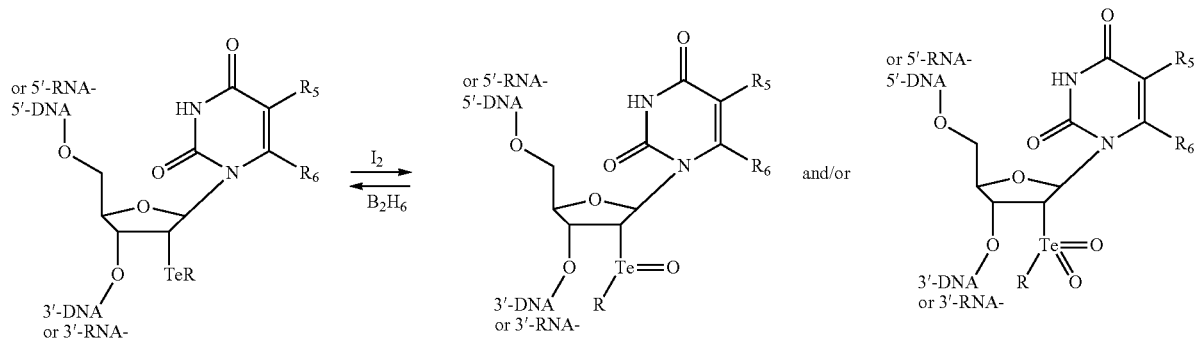

in which the 2'-telluride DNA (or RNA) can be oxidized to the 2'-telluroxide DNA (or RNA) and/or 2'-tellurone DNA (or RNA) by $I_2$, and the 2'-telluroxide DNA (or RNA) and/or 2'-tellurone DNA (or RNA) can be reduced back to the 2'-telluride DNA (or RNA) by $B_2H_6$.

Another general reaction scheme for the preparation of the compound of formula I or the derivative of such compound is a preparation wherein the 2'-Te-DNAs (or RNAs) can be cleaved at the 2' and 3' positions under the treatment of $B_2H_6$ or $I_2$ to form fragmented product; or can be cleaved at the 1' and 2' positions under the treatment of $B_2H_6$ to form debased product, according to scheme 5:

Scheme 5

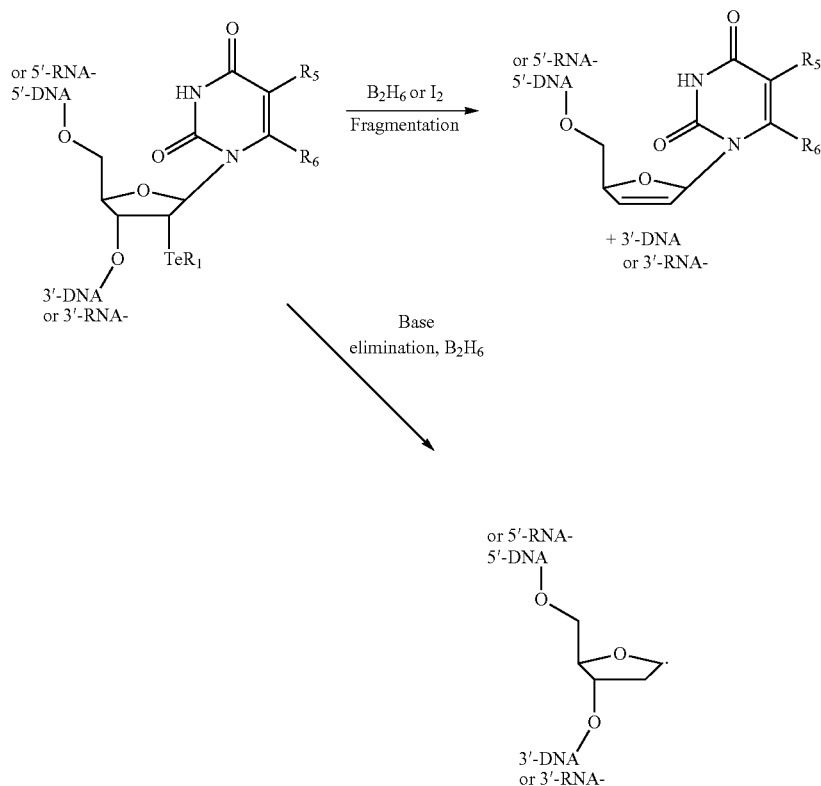

Figure 3:
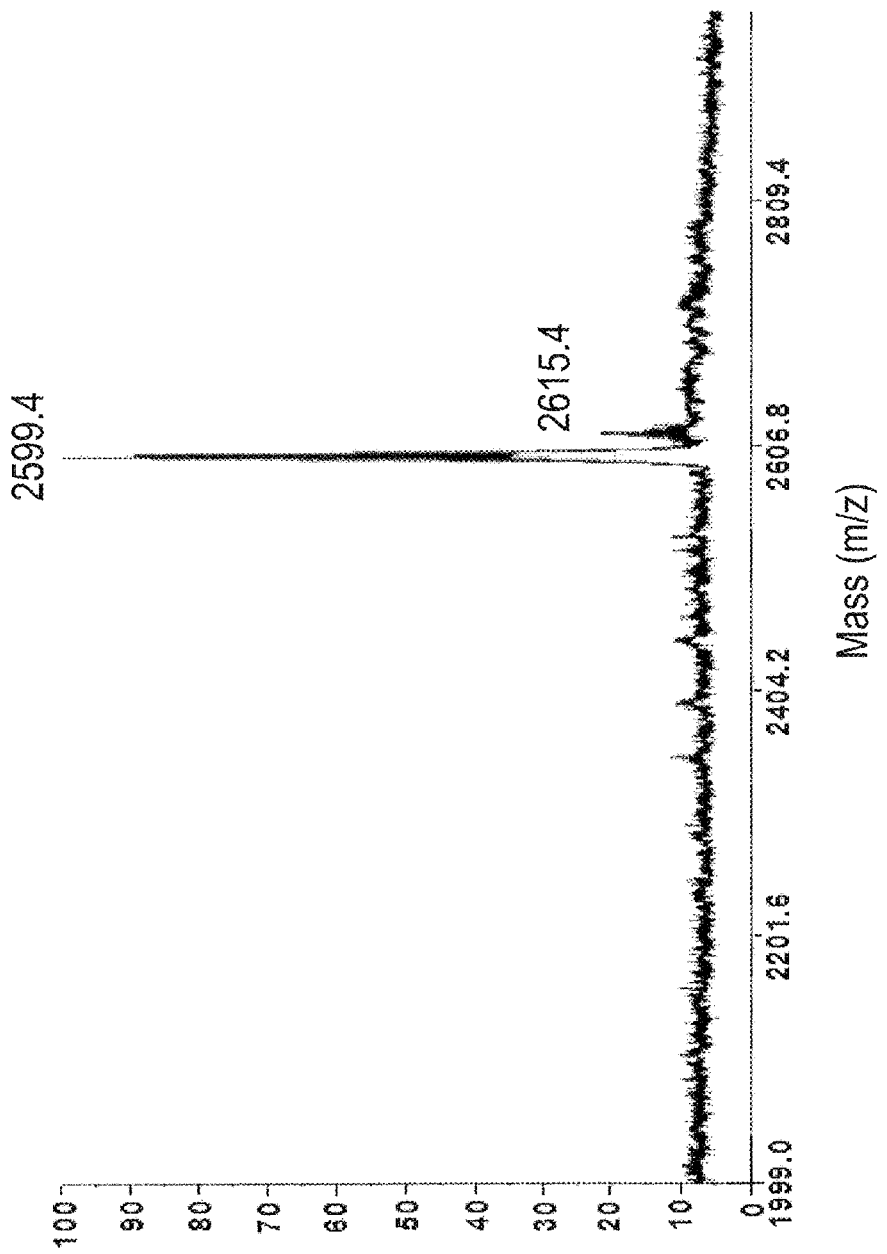
FIG. 3. A representation of MALDI-TOF MS analysis of the Te-DNA [5'-G(2'-TePh-dU)GTACAC-3'] according to some forms of the disclosure.
Figure 4:
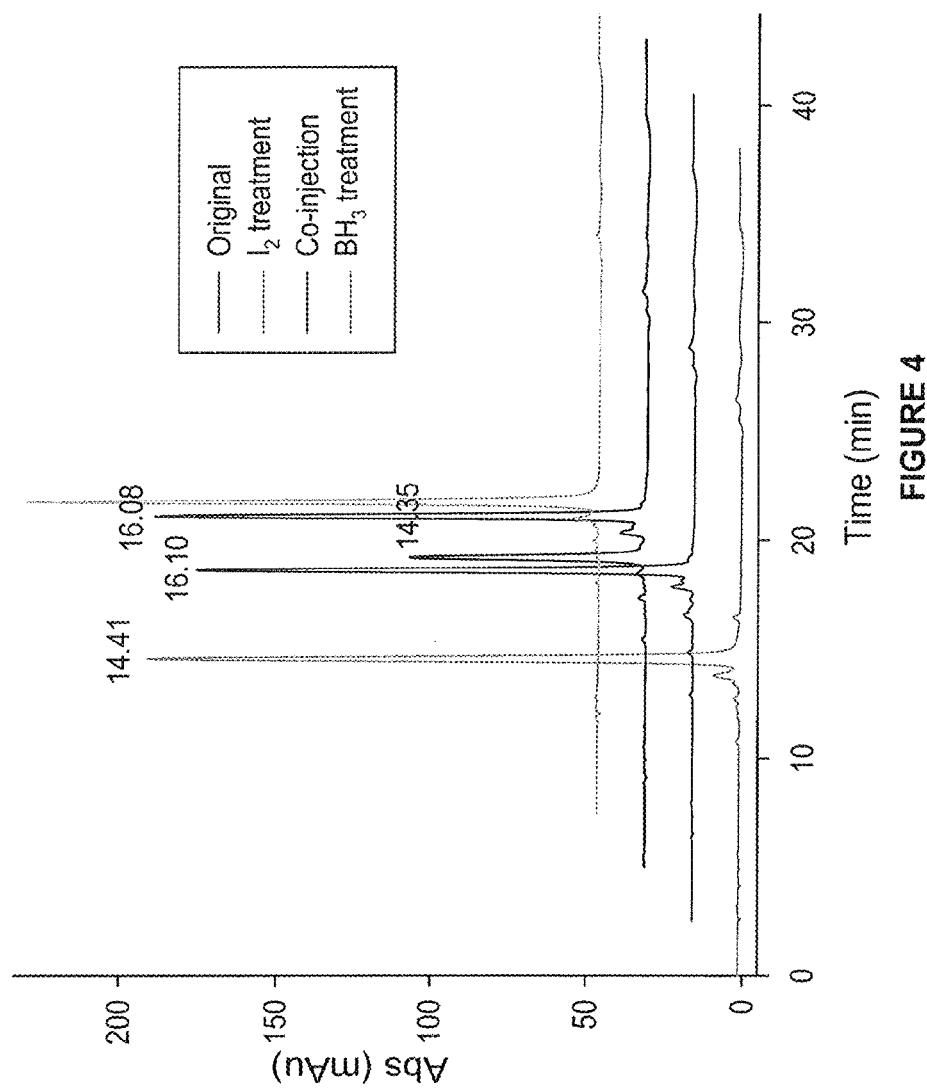
FIG. 4. A representation of redox property of 2'-TePh-DNA 8-mer [5'-G(2'-TePh-dU)GTACAC] with the $I_2$ and $B_2H_6$ treatments. Red: the non-oxidized Te-DNA; blue: the Te-DNA after $I_2$ treatment; black: the co-injection of the non-oxidized and oxidized Te-DNAs; purple: the oxidized Te-DNA after $B_2H_6$ treatment.
Figure 5:
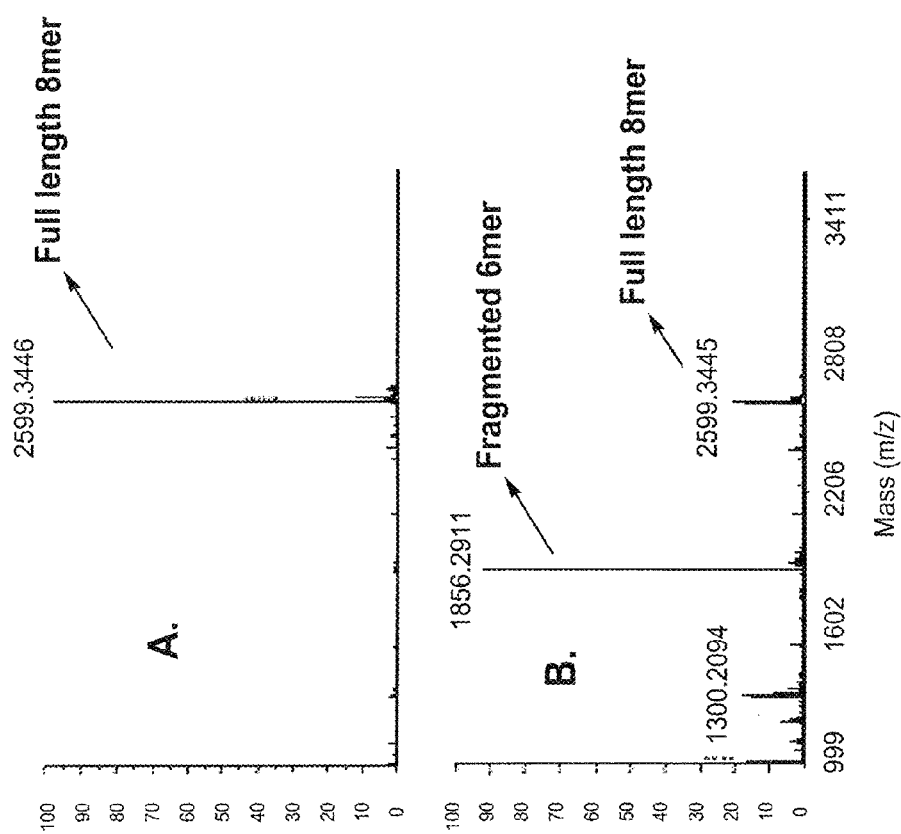
FIG. 5. A representation of cleavage of the 2'-TePh-modified DNA 8-mer [5'-G(2'-TePh-dU)GTACAC-3]. (A) before heating, the molecular formula: $C_{83}H_{101}N_{30}O_{46}P_7Te$, [M–H$^+$]$^-$: 2599.3; (B) after fragmentation with either $I_2$ or $B_2H_6$ at 50° C., the fragmented 6-mer (5'-p-GTACAC-3'); the 6-mer molecular formula: $C_{58}H_{74}N_{23}O_{36}P_6$, [M–H$^+$]$^-$: 1856.2 calculated; its observed molecular mass peak: 1856.3.
Figure 11:
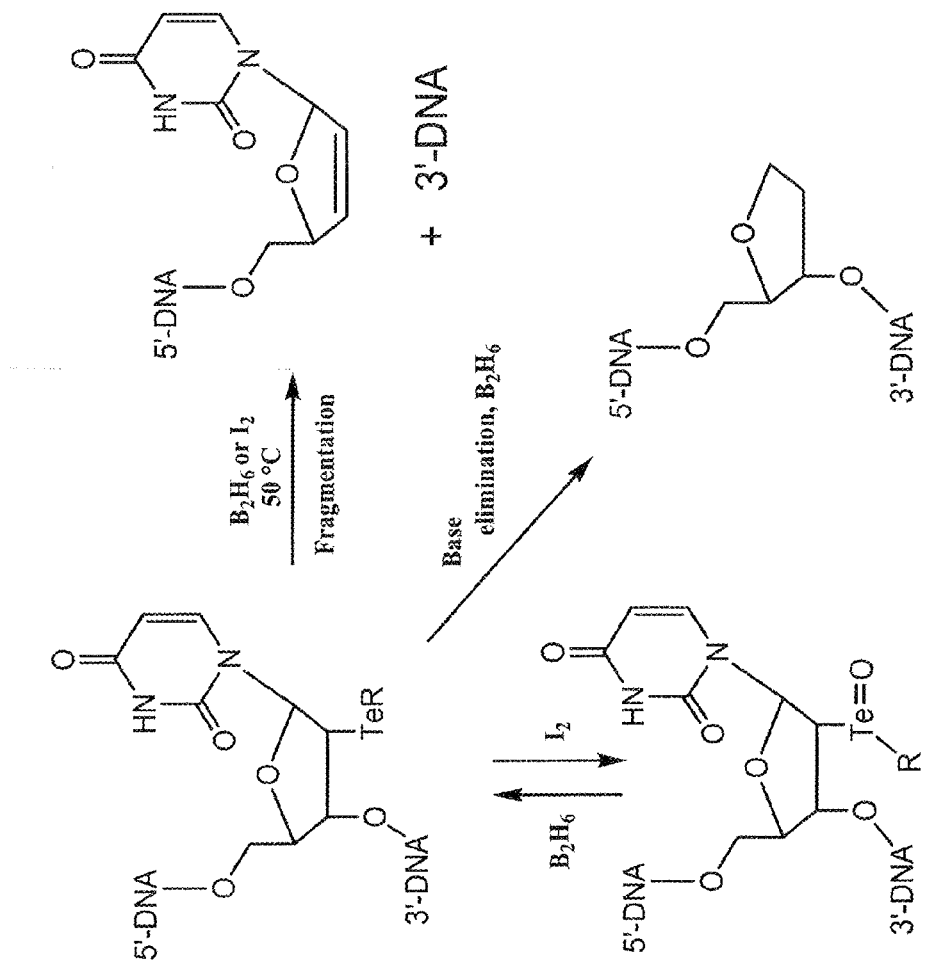
FIG. 11. A representation of a synthetic scheme with redox and fragmentation of DNA oligonucleotides containing 2'-Te functionalities according to some forms of the invention.
Figure 12:
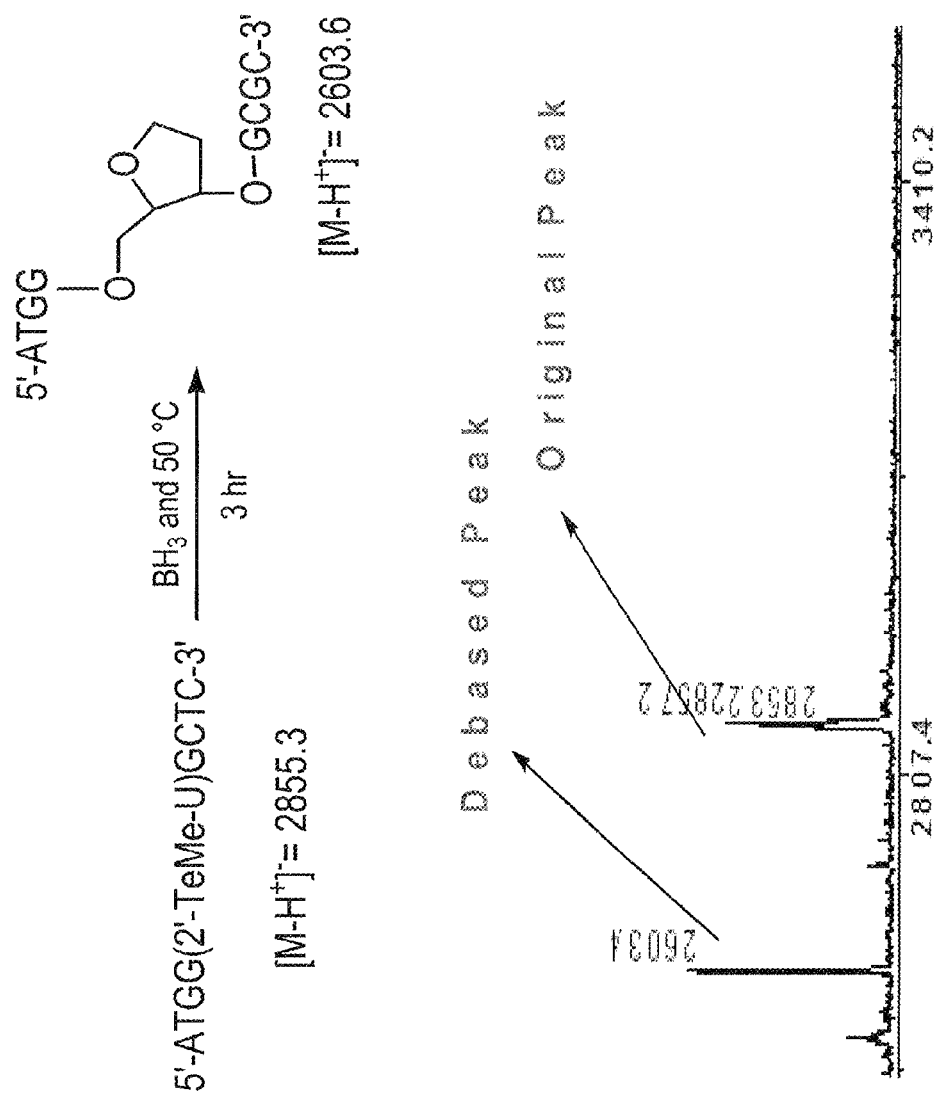
FIG. 12. A representation of MALDI-TOF analysis of the reductive debase of the 2'-TeMe modified sequence 5'-ATGG (2'-TeMe-U)GCTC-3'.

It is noteworthy mentioning that a small portion of the Te-DNAs (or RNAs) are oxidized to the telluroxides (or tellurone) DNAs (or RNAs) during the solid-phase synthesis and purification (FIG. 3). FIG. 3 shows MALDI-TOF MS analysis of the Te-DNA [5'-G(2'-TePh-dU)GTACAC-3'] according to a form of the disclosure. The peak with a mass of M+16 (2614.4) in FIG. 3 indicates formation of the telluroxide. However, the telluroxides can be reduced back to the tellurides. Using the purified 2'-Te-DNAs, it was demonstrated that at the room temperature, the telluride DNA can be oxidized to the telluroxide DNA by $I_2$, and the oxidized DNA (or RNA) can be reduced back to the telluride DNA by $B_2H_6$ treatment (FIG. 11 and FIG. 4). This provides a useful approach to recover the oxidized Te-DNA during the DNA synthesis, and also allows investigation of the redox property of the Te-DNA. Interestingly, under heating (50° C.), it was observed a site-specific cleavage of the 2'-TePh DNA at the modification site in the presence of either $B_2H_6$ or $I_2$ (FIG. 11 and FIG. 5). This result is consistent with the observation of the 2',3' elimination of the Te-nucleosides [J. Sheng, A. E. Hassan, Z. Huang, *J. Org. Chem.* 2008, 73, 3725-3729]. This site-specific fragmentation provides a good model for DNA damage study. Interestingly, in a 2'-TeMe-modified DNA 9-mer [5'-ATGG(2'-TeMe-dU)GCTC-3'], the debase reaction (1',2' elimination) was observed (FIG. 11 and FIG. 12), and the formed C—C double bond was further reduced by $B_2H_6$. It was found that the 2'-Te-Ph functionality generates the fragmented product, while the 2'-Te-Me functionality creates the debased product. These two Te-DNA modification strategies can be useful in investigation of the site-specific DNA cleavage and base damage formation [J. Chen, J. Stubbe, *Biochem.* 2004, 43, 5278-5286; K. Usui, M. Aso, M. Fukuda, H. Suemune, *J. Org. Chem.* 2008, 73, 241-248; M. J. Maul, T. R. M. Barends, A. F. Glas, M. J. Cryle, T. Domratcheva, S. Schneider, I. Schlichting, T. Carell, Angew. Chem. Int. Ed. 2008, 47, 10076-10080].

Methods

The above-described compounds, derivatives of the compounds, or the pharmaceutically acceptable salt of the compounds and the derivatives are useful for counducting drug discovery and research. Accordingly, in some forms, disclosed are methods of counducting drug discovery and research wherein said methods comprises applying the compound of formula I, and/or the derivative of the compound in an investigation. In some other forms, the investigation involves studying DNA (or RNA) duplex flexibility, methylation function, or base-stacking interaction in a DNA (or RNA) duplex. In some other forms, the investigation involves probing crystal structure, function studies, STM imaging, and nanoelectronic materials of nucleic acids. In some other forms, the investigation involves probing the DNA (or RNA) fragmentattion and nucleobase damage by subjecting the compound of 2'-Te-DNAs (or RNAs) under reductively or oxadatively cleavage. In some other forms, the investigation involves probing DNA and/or RNA polymerization and/or catalysis by studying the UV-melting temperature of 2'-Te-DNAs (or RNAs) in accordance to the variation of the Te location in DNA (or RNA), the protective group to Te, the DNA (or RNA) as a self-complementary or non self-complementary duplex. In some other forms, the investigation involves probing the formation of DNA or RNA loop, bulge and other secondary or 3D structures by studying the UV-melting temperature of 2'-Te-DNAs (or RNAs) in accordance to the variation of the Te location in DNA (or RNA), the protective group to Te, the DNA (or RNA) as a self-complementary or non self-complementary duplex. The DNAs and/or RNAs is selected from the group consisting of siRNAs, microRNAs and antisense DNAs.

A. Definitions

1. A, an, the

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

2. Cell

The term "cell" as used herein also refers to individual cells, cell lines, or cultures derived from such cells. A "culture" refers to a composition comprising isolated cells of the same or a different type. The term co-culture is used to designate when more than one type of cell are cultured together in the same dish with either full or partial contact with each other.

3. Complex

The term complex as used herein refers to the association of a compound with an ion channel or enzyme for which the compound has a binding affinity.

4. Compound

For the purposes of the present disclosure the terms "compound," "analog," and "composition of matter" stand equally well for the chemical entities described herein, including all enantiomeric forms, diastereomeric forms, salts, and the like, and the terms "compound," "analog," and "composition of matter" are used interchangeably throughout the present specification.

5. Comprise

Throughout the description and claims of this specification, the word "comprise" and variations of the word, such as "comprising" and "comprises," means "including but not limited to," and is not intended to exclude, for example, other additives, components, integers or steps.

6. Components

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific form or combination of forms of the disclosed methods.

7. Chemistry

The term "alkyl" refers to a linear or branched-chain saturated hydrocarbyl substituent (i.e., a substituent obtained from a hydrocarbon by removal of a hydrogen) containing from one to twenty carbon atoms; in some forms from one to twelve carbon atoms; in some forms, from one to ten carbon atoms; in some forms, from one to six carbon atoms; and in some forms, from one to four carbon atoms. Examples of such substituents include methyl, ethyl, propyl (including n-propyl and isopropyl), butyl (including n-butyl, isobutyl, sec-butyl and tert-butyl), pentyl, iso-amyl, hexyl and the like.

The term "alkenyl" refers to a linear or branched-chain hydrocarbyl substituent containing one or more double bonds and from two to twenty carbon atoms; in some forms, from two to twelve carbon atoms; in some forms, from two to six carbon atoms; and in some forms, from two to four carbon atoms. Examples of alkenyl include ethenyl (also known as vinyl), allyl, propenyl (including 1-propenyl and 2-propenyl) and butenyl (including 1-butenyl, 2-butenyl and 3-butenyl). The term "alkenyl" embraces substituents having "cis" and "trans" orientations, or alternatively, "E" and "Z" orientations.

The term "benzyl" refers to methyl radical substituted with phenyl, i.e., the following structure:

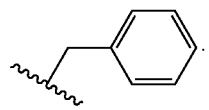

The term "cycloalkyl" refers to a saturated carbocyclic substituent having three to fourteen carbon atoms. In some forms, a cycloalkyl substituent has three to ten carbon atoms. Examples of cycloalkyl include cyclopropyl, cyclobutyl, cyclopentyl and cyclohexyl.

The term "cycloalkyl" also includes substituents that are fused to a $C_6$-$C_{10}$ aromatic ring or to a 5-10-membered heteroaromatic ring, wherein a group having such a fused cycloalkyl group as a substituent is bound to a carbon atom of the cycloalkyl group. When such a fused cycloalkyl group is substituted with one or more substituents, the one or more substituents, unless otherwise specified, are each bound to a carbon atom of the cycloalkyl group. The fused $C_6$-$C_{10}$ aromatic ring or to a 5-10-membered heteroaromatic ring can be optionally substituted with halogen, $C_1$-$C_6$ alkyl, $C_3$-$C_{10}$ cycloalkyl, or =O.

The term "cycloalkenyl" refers to a partially unsaturated carbocyclic substituent having three to fourteen carbon atoms, typically three to ten carbon atoms. Examples of cycloalkenyl include cyclobutenyl, cyclopentenyl, and cyclohexenyl.

A cycloalkyl or cycloalkenyl can be a single ring, which typically contains from 3 to 6 ring atoms. Examples include cyclopropyl, cyclobutyl, cyclopentyl, cyclopentenyl, cyclopentadienyl, cyclohexyl, cyclohexenyl, cyclohexadienyl, and phenyl. Alternatively, 2 or 3 rings can be fused together, such as bicyclodecanyl and decalinyl.

The term "aryl" refers to an aromatic substituent containing one ring or two or three fused rings. The aryl substituent can have six to eighteen carbon atoms. As an example, the aryl substituent can have six to fourteen carbon atoms. The term "aryl" can refer to substituents such as phenyl, naphthyl and anthracenyl. The term "aryl" also includes substituents such as phenyl, naphthyl and anthracenyl that are fused to a $C_4$-$C_{10}$ carbocyclic ring, such as a $C_5$ or a $C_6$ carbocyclic ring, or to a 4-10-membered heterocyclic ring, wherein a group having such a fused aryl group as a substituent is bound to an aromatic carbon of the aryl group. When such a fused aryl group is substituted with one more substituents, the one or more substituents, unless otherwise specified, are each bound to an aromatic carbon of the fused aryl group. The fused $C_4$-$C_{10}$ carbocyclic or 4-10-membered heterocyclic ring can be optionally substituted with halogen, $C_1$-$C_6$ alkyl, $C_3$-$C_{10}$ cycloalkyl, or =O. Examples of aryl groups include accordingly phenyl, naphthalenyl, tetrahydronaphthalenyl (also known as "tetralinyl"), indenyl, isoindenyl, indanyl, anthracenyl, phenanthrenyl, benzonaphthenyl (also known as "phenalenyl"), and fluorenyl.

The term "hydrogen" refers to hydrogen substituent, and can be depicted as —H.

The term "hydroxy" refers to —OH. When used in combination with another term(s), the prefix "hydroxy" indicates that the substituent to which the prefix is attached is substituted with one or more hydroxy substituents. Compounds bearing a carbon to which one or more hydroxy substituents include, for example, alcohols, enols and phenol.

The term "hydroxyalkyl" refers to an alkyl that is substituted with at least one hydroxy substituent. Examples of hydroxyalkyl include hydroxymethyl, hydroxyethyl, hydroxypropyl and hydroxybutyl.

The term "nitro" means —$NO_2$.

The term "cyano" (also referred to as "nitrile") —CN, which also can be depicted:

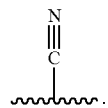

The term "carbonyl" means —C(O)—, which also can be depicted as:

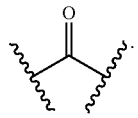

The term "amino" refers to —$NH_2$.

The term "alkylamino" refers to an amino group, wherein at least one alkyl chain is bonded to the amino nitrogen in place of a hydrogen atom. Examples of alkylamino substituents include monoalkylamino such as methylamino (exemplified by the formula —$NH(CH_3)$), which can also be depicted:

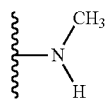

and dialkylamino such as dimethylamino, exemplified by the formula —$N(CH_3)_2$, which can also be depicted:

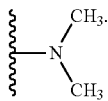

The term "aminocarbonyl" means —C(O)—NH$_2$, which also can be depicted as:

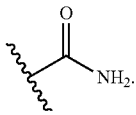

The term "halogen" refers to fluorine (which can be depicted as —F), chlorine (which can be depicted as —Cl), bromine (which can be depicted as —Br), or iodine (which can be depicted as —I). In some forms, the halogen is chlorine. In some forms, the halogen is a fluorine.

The prefix "halo" indicates that the substituent to which the prefix is attached is substituted with one or more independently selected halogen substituents. For example, haloalkyl refers to an alkyl that is substituted with at least one halogen substituent. Where more than one hydrogen is replaced with halogens, the halogens can be identical or different. Examples of haloalkyls include chloromethyl, dichloromethyl, difluorochloromethyl, dichlorofluoromethyl, trichloromethyl, 1-bromoethyl, fluoromethyl, difluoromethyl, trifluoromethyl, 2,2,2-trifluoroethyl, difluoroethyl, pentafluoroethyl, difluoropropyl, dichloropropyl, and heptafluoropropyl. Illustrating further, "haloalkoxy" refers to an alkoxy that is substituted with at least one halogen substituent. Examples of haloalkoxy substituents include chloromethoxy, 1-bromoethoxy, fluoromethoxy, difluoromethoxy, trifluoromethoxy (also known as "perfluoromethyloxy"), and 2,2,2-trifluoroethoxy. It should be recognized that if a substituent is substituted by more than one halogen substituent, those halogen substituents can be identical or different (unless otherwise stated).

The term "oxo" refers to =O.

The term "oxy" refers to an ether substituent, and can be depicted as —O—.

The term "alkoxy" refers to an alkyl linked to an oxygen, which can also be represented as —O—R, wherein the R represents the alkyl group. Examples of alkoxy include methoxy, ethoxy, propoxy and butoxy.

The term "alkylthio" means —S-alkyl. For example, "methylthio" is —S—CH$_3$. Other examples of alkylthio include ethylthio, propylthio, butylthio, and hexylthio.

The term "alkylcarbonyl" means —C(O)-alkyl. For example, "ethylcarbonyl" can be depicted as:

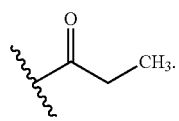

Examples of other alkylcarbonyl include methylcarbonyl, propylcarbonyl, butylcarbonyl, pentylcabonyl, and hexylcarbonyl.

The term "aminoalkylcarbonyl" means —C(O)-alkyl-NH$_2$. For example, "aminomethylcarbonyl" can be depicted as:

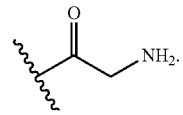 [SMILES: *C(=O)CN]

The term "alkoxycarbonyl" means —C(O)-alkyl. For example, "ethoxycarbonyl" can be depicted as:

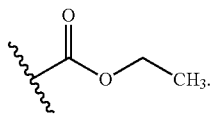 [SMILES: *C(=O)OCC]

Examples of other alkoxycarbonyl include methoxycarbonyl, ethoxycarbonyl, propoxycarbonyl, butoxycarbonyl, pentoxycarbonyl, and hexyloxycarbonyl. In some forms, where the carbon atom of the carbonyl is attached to a carbon atom of a second alkyl, the resulting functional group is an ester.

The terms "thio" and "thia" mean a divalent sulfur atom and such a substituent can be depicted as —S—. For example, a thioether is represented as "alkyl-thio-alkyl" or, alternatively, alkyl-S-alkyl.

The term "thiol" refers to a sulfhydryl substituent, and can be depicted as —SH.

The term "thione" refers to =S.

The term "sulfonyl" refers to —S(O)$_2$—, which also can be depicted as:

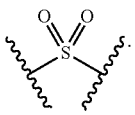

Thus, for example, "alkyl-sulfonyl-alkyl" refers to alkyl-S(O)$_2$-alkyl. Examples of alkylsulfonyl include methylsulfonyl, ethylsulfonyl, and propylsulfonyl.

The term "aminosulfonyl" means —S(O)$_2$—NH$_2$, which also can be depicted as:

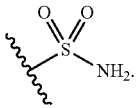

The term "sulfinyl" or "sulfoxido" means —S(O)—, which also can be depicted as:

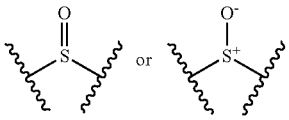

Thus, for example, "alkylsulfinylalkyl" or "alkylsulfoxidoalkyl" refers to alkyl-S(O)-alkyl. Exemplary alkylsulfinyl groups include methylsulfinyl, ethylsulfinyl, butylsulfinyl, and hexylsulfinyl.

8. Control

The terms "control" or "control levels" or "control cells" are defined as the standard by which a change is measured, for example, the controls are not subjected to the experiment, but are instead subjected to a defined set of parameters, or the controls are based on pre- or post-treatment levels. They can either be run in parallel with or before or after a test run, or they can be a pre-determined standard.

9. Higher

The terms "higher," "increases," "elevates," or "elevation" or like terms or variants of these terms, refer to increases above basal levels, e.g., as compared a control. The terms "low," "lower," "reduces," "decreases" or "reduction" or variation of these terms, refer to decreases below basal levels, e.g., as compared to a control. For example, basal levels are normal in vivo levels prior to, or in the absence of, or addition of an agent such as an agonist or antagonist to activity. For example, decreases or increases can be used to describe the binding of a molecule to a receptor. In this context, decreases would describe a situation of where the binding could be defined as having a Kd of $10^{-9}$ M, if this interaction decreased, meaning the binding lessened, the Kd could decrease to $10^{-6}$ M. It is understood that wherever one of these words is used it is also disclosed that it could be 1%, 5%, 10%, 20%, 50%, 100%, 500%, or 1000% increased or decreased from a control.

10. Inhibit

By "inhibit" or other forms of inhibit means to hinder or restrain a particular characteristic. It is understood that this is typically in relation to some standard or expected value, in other words it is relative, but that it is not always necessary for the standard or relative value to be referred to. For example, "inhibits phosphorylation" means hindering or restraining the amount of phosphorylation that takes place relative to a standard or a control.

11. Maintaining

The word "maintaining" or like words refers to continuing a state. In the context of a treatment, maintaining can be refer to less than 20%, 15%, 10%, 9%, 8%, 7%, 6%, 5%, 4%, 3%, 2%, 1%, or 0.1% change from a control, such a basal level, often a level in the absence of a treatment or in the presence of treatment with a placebo or standard.

12. Material

Material is the tangible part of something (chemical, biochemical, biological, or mixed) that goes into the makeup of a physical object.

13. Modulate

The term modulate or like terms refers to its standard meaning of increasing or decreasing.

14. Substance

A substance or like terms is any physical object. A material is a substance. Molecules, ligands, markers, cells, proteins, DNA and RNA can be considered substances. A machine or an article would be considered to be made of substances, rather than considered a substance themselves.

15. Molecule

As used herein, the terms "molecule" or like terms refers to a biological or biochemical or chemical entity that exists in the form of a chemical molecule or molecule with a definite molecular weight. A molecule or like terms is a chemical, biochemical or biological molecule, regardless of its size.

Many molecules are of the type referred to as organic molecules (molecules containing carbon atoms, among others, connected by covalent bonds), although some molecules do not contain carbon (including simple molecular gases such as molecular oxygen and more complex molecules such as some sulfur-based polymers). The general term "molecule" includes numerous descriptive classes or groups of molecules, such as proteins, nucleic acids, carbohydrates, steroids, organic pharmaceuticals, small molecule, receptors, antibodies, and lipids. When appropriate, one or more of these more descriptive terms (many of which, such as "protein," themselves describe overlapping groups of molecules) will be used herein because of application of the method to a subgroup of molecules, without detracting from the intent to have such molecules be representative of both the general class "molecules" and the named subclass, such as proteins. Unless specifically indicated, the word "molecule" would include the specific molecule and salts thereof, such as pharmaceutically acceptable salts.

16. Optionally

"Optional" or "optionally" means that the subsequently described event or circumstance may or may not occur, and that the description includes instances where said event or circumstance occurs and instances where it does not.

17. Prevent

By "prevent" or other forms of prevent means to stop a particular characteristic or condition. Prevent does not require comparison to a control as it is typically more absolute than, for example, reduce or inhibit. As used herein, something could be reduced but not inhibited or prevented, but something that is reduced could also be inhibited or prevented. Similarly, something could be reduced and inhibited, but not prevented. It is understood that where reduce, inhibit or prevent are used, unless specifically indicated otherwise, the use of the other two words is also expressly disclosed. Thus, if inhibits phosphorylation is disclosed, then reduces and prevents phosphorylation are also disclosed.

18. Ranges

Ranges can be expressed herein as from "about" one particular value, and/or to "about" another particular value. When such a range is expressed, some forms includes from the one particular value and/or to the other particular value. Similarly, when values are expressed as approximations, by use of the antecedent "about," it will be understood that the particular value forms some forms. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data are provided in a number of different formats, and that this data, represents endpoints and starting points, and ranges for any combination of the data points. For example, if a particular datum point "10" and a particular datum point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

19. Reduce

By "reduce" or other forms of reduce means lowering of an event or characteristic. It is understood that this is typically in relation to some standard or expected value, in other words it is relative, but that it is not always necessary for the standard or relative value to be referred to. For example, "reduces phosphorylation" means lowering the amount of phosphorylation that takes place relative to a standard or a control.

20. References

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

21. Specifically interacts

Specifically interacts or like terms means that the interaction is beyond a background interaction. The background interaction can be determined by for example looking at the interaction with serum albumin.

22. Subject

As used throughout, by a "subject" is meant an individual. Thus, the "subject" can include, for example, domesticated animals, such as cats, dogs, etc., livestock (e.g., cattle, horses, pigs, sheep, goats, etc.), laboratory animals (e.g., mouse, rabbit, rat, guinea pig, etc.) mammals, non-human mammals, primates, non-human primates, rodents, birds, reptiles, amphibians, fish, and any other animal. The subject can be a mammal such as a primate or a human. The subject can also be a non-human.

23. Tissue

Tissue or like terms refers to a collection of cells. Typically a tissue is obtained from a subject.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

A. Materials and General Procedures

Most solvents and reagents were purchased from Sigma-Aldrich or VWR without further purification unless mentioned otherwise. Dimethyl ditelluride was purchased from Organometallics. Triethylamine (TEA) and THF was dried over KOH (s) and sodium metal respectively and distilled under argon. When necessary, solid reagents were dried under high vacuum. Reactions with compounds sensitive to air or moisture were performed under argon. Solvent mixtures are indicated as volume/volume ratios. Thin layer chromatography (TLC) was run on Merck 60 F254 plates (0.25 mm thick; Rf values in the text are for the title products), and visualized under UV-light or by a Ce—Mo staining solution (phosphomolybdate, 25 g; $Ce(SO_4)_2 \cdot 4H_2O$, 10 g; $H_2SO_4$, 60 mL, conc.; $H_2O$, 940 mL) with heating. Flash chromatography was performed using Fluka silica gel 60 (mesh size 0.040-0.063 mm). $^1H$ and $^{13}C$ spectra were recorded using Bruker-400 (400 and 100 MHz). All chemical shifts are in ppm relative to tetramethylsilane and all coupling constants (J) are in Hz. High resolution mass spectrum (HRMS) analysis was performed at Scripps and Georgia State University Mass Spectrometry Center.

B. Preparation of Compounds of Formula (I)

The following are examples of preparation of compounds of formula (I), or derivatives of the compound of formula (I). These examples are intended to be purely exemplary and are not intended to limit the disclosure.

2'-deoxy-2'-phenyltellanyl-5'-O-(4,4'-dimethoxytrityl)-uridine (4a) and 2'-deoxy-2'-phenyltellanyl-5'-O-(4,4'-dimethoxytrityl)-5-methyluridine (4b) in FIG. 8

To a stirred suspension of $NaBH_4$ (6.2 mg, 0.15 mmol) in anhydrous THF (5 mL), under argon at 0° C., the THF solution of diphenylditelluride (0.2 g, 0.5 mmol in 5 mL) was added, followed by several drops of dry ethanol until bubble formed and the solution turned colorless. To this solution the starting material 3a or 3b (0.285 g and 0.292 g separately, 0.5 mmol, dissolved in 5 mL of THF) was added and the reaction was slowly warmed up to room temperature and then into 50° C. for three hours, which monitored by TLC. The solvent was then evaporated. The residue was dissolved in $CH_2Cl_2$ (20 mL) and washed with water (3×20 mL) The $CH_2Cl_2$ solution was dried ($MgSO_4$), concentrated and the crude product was purified by silica gel column chromatography with 0-3% methanol in $CH_2Cl_2$ to give compound 4a and 4b as slight yellow solid (4a: 310 mg, 80% yield, 4b: 292 mg, 78% yield). 4a: $^1H$ NMR (400 MHz, $CDCl_3$, 25° C.): δ=3.45-3.46 (m, 2H), 3.82 (s, 3H), 3.92-3.95 (m, 1H), 4.24 (m, 1H), 4.54-4.57 (m, 1H), 5.12 (d, J=8 Hz, 1H), 6.63 (d, J=9.2 Hz, 1H), 6.81-6.86 (m, 4H), 7.19-7.37 (m, 12H), 7.45 (d, J=8 Hz, 1H), 7.82 (m, 2H); $^{13}C$ NMR (100 MHz, $CDCl_3$, 25° C.): δ=36.9, 55.3, 63.9, 85.5, 87.2, 91.6, 102.5, 109.6, 113.3, 127.2, 127.8, 128.1, 128.1, 128.7, 129.5, 130.1, 135.2, 140.2, 144.2, 150.2, 158.7, 162.7; HRMS: m/z: calcd for $C_{36}H_{34}N_2O_7TeNa$: 759.1326. found: 759.1316 [M+Na]$^+$. 4b: $^1H$ NMR (400 MHz, $CDCl_3$, 25° C.): δ=1.21 (s, 3H), 3.35-3.52 (m, 2H), 3.81 (s, 6H), 3.98-4.01 (m, 1H), 4.22 (m, 1H), 4.55 (m, 1H), 6.69 (d, J=10 Hz, 1H), 6.81-6.84 (m, 4H), 7.16-7.35 (m, 15H), 7.83 (m, 2H), 8.17 (b, 1H); $^{13}C$ NMR (100 MHz, $CDCl_3$, 25° C.): δ=11.5, 36.8, 55.3, 63.9, 85.2, 87.2, 91.0, 109.5, 111.3, 113.3, 127.2, 128.0, 128.1, 128.6, 129.6, 130.1, 135.0, 135.2, 140.3, 144.2, 150.4, 158.8, 163.1; HRMS: m/z: calcd for $C_{37}H_{36}N_2O_7TeNa$: 773.1477, found: 773.1475 [M+Na$^+$]$^+$.

2'-phenyltellanyl-5'-O-(4,4'-dimethoxytriphenylmethyl)-uridine 3'-O-(2-cyanoethyl)diisopropylamino phosphoramidite (5a) and 2'-phenyltellanyl-5'-O-(4, 4'-dimethoxytriphenylmethyl)-5-methyluridine 3'-O-(2-cyanoethyl)diisopropylamino phosphoramidite (5b) in FIG. 8

To the flask (25 mL) containing 4a or 4b (500 mg and 510 mg separately, 0.68 mmol) under argon, dry methylene chloride (2.5 mL), N,N-diisopropylethylamine (0.17 mL, 1.03 mmol, 1.5 eq.), and 2-cyanoethyl N,N-diisopropyl-chlorophosphoramidite (195 mg, 0.83 mmol, 1.2 eq.) were added sequentially. The reaction mixture was stirred at −10° C. in an ice-salt bath under argon for 10 minutes, followed by removal of the bath. The reaction was completed in 45 minutes at room temperature (indicated by TLC, 5% MeOH in $CH_2Cl_2$), generating a mixture of two diastereomers. The reaction was then quenched with $NaHCO_3$ (2 mL, sat.), stirred for 5 min, and the product was then extracted with $CH_2Cl_2$ (3×5 mL). The combined organic layer was washed with NaCl (10 mL, sat.) and dried over $MgSO_4$ (s) for 20 min, followed by filtration. The solvent was then evaporated under reduced pressure and the crude product was re-dissolved in $CH_2Cl_2$ (2 mL). This solution was added drop-wise to petroleum ether (200 mL) under vigorous stirring, generating a white precipitate. The petroleum ether solution was decanted carefully. The crude product was re-dissolved again in $CH_2Cl_2$ (2 mL) and then loaded into an $Al_2O_3$ column (neutral) that was equilibrated with $CH_2Cl_2$/Hexanes (1:1). The column was eluded with a gradient of $CH_2Cl_2$ to $CH_2Cl_2$/EtOAc (7:3). After solvent evaporation and dry over high vacuum, the pure 5a and 5b (570 mg) were obtained as a white foamy products (88-90% yield). 5a: $^1H$ NMR (400 MHz, $CDCl_3$, 25° C.): δ=1.13-1.35 (m, 24H), 2.37 and 2.68 (2×t, J=6.4 Hz, 4H), 3.38-3.69 (m, 12H), 3.83 (s, 12H), 3.90-4.03 (m, 2H), 4.32 and 4.38 (2×m, 2H), 4.67-4.82 (m, 2H), 4.95 and 5.00 (2x d, J=8 Hz, 2H), 6.73 and 6.75 (2x d, J=5.8 Hz, 2H), 6.83-6.86 (m, 8H), 7.16-7.37 (m, 26H), 7.76 (br, 2H), 7.81-7.85 (m, 4H); $^{13}C$ NMR (100 MHz, $CDCl_3$, 25° C.): δ=20.13, 20.20, 20.44, 20.51, 24.50, 24.61, 24.69, 25.23, 33.85, 34.43, 43.36, 43.40, 43.49, 43.52, 55.29, 57.68, 57.87, 59.04, 59.23, 63.58, 63.73, 74.91 and 75.09, 84.97, 87.29, 89.38, 111.69, 113.46, 117.29, 126.99, 127.81, 128.54, 130.21, 130.42, 135.22, 135.40, 135.44, 144.10, 150.37, 158.85, 163.34; $^{31}P$ NMR (160 MHz, $CDCl_3$, 25° C.): δ=148.6, 149.2; HRMS: m/z: calcd for $C_{45}H_{52}N_4O_8PTe$: 937.2579. found: 937.2578 [M+H]$^+$. 5b: $^1H$ NMR (400 MHz, $CDCl_3$, 25° C.): δ=1.10-1.42 (m, 24H), 2.34 and 2.66 (2×t, J=6.4 Hz, 4H), 3.35-3.69 (m, 12H), 3.83 (s, 12H), 3.92-4.05 (m, 2H), 4.31 and 4.37 (2×m, 2H), 4.65-4.82 (m, 2H), 6.71 and 6.74 (2x d, J=5.8 Hz, 2H), 6.84-6.86 (m, 8H), 7.16-7.37 (m, 26H), 7.77 (br, 2H), 7.80-7.84 (m, 4H); $^{13}C$ NMR (100 MHz, $CDCl_3$, 25° C.): δ=11.69, 20.12, 20.22, 20.43, 20.53, 24.49, 24.60, 24.67, 25.24, 33.85, 34.43, 43.37, 43.40, 43.49, 43.53, 55.27, 57.67, 57.88, 59.05, 59.25, 63.57, 63.74, 74.92 and 75.09, 84.97, 87.27, 89.38, 111.68, 113.45, 117.28, 126.98, 127.81, 128.54, 130.20, 130.39, 135.24, 135.38, 135.42, 144.11, 150.35, 158.87, 163.36; $^{31}P$ NMR (160 MHz, $CDCl_3$, 25° C.): δ=148.4, 149.3; HRMS: m/z: calcd for $C_{46}H_{53}N_4O_8PTeNa$: 973.2561. found: 973.2560 [M+Na]$^+$.

(R)-5-(4,4'-dimethoxytrityloxymethyl)-2,3-dihydro-furan-4-ol (6) in FIG. 9

To a stirred suspension of $NaBH_4$ (12 mg, 0.3 mmol) in dry THF (5 mL), under argon, dimethyl ditelluride (0.05 mL, 0.3 mmol) was added, followed by several drops of dry ethanol until bubble formed. The suspension was heated to 50° C., followed by the addition of THF solution of starting material 3a (320 mg, 0.6 mmol). The mixture was heated for three hours at this temperature under argon. The solvent was then evaporated and the residue was dissolved in $CH_2Cl_2$ (20 mL) and washed with water (3×20 mL) The $CH_2Cl_2$ layer was dried $MgSO_4$, concentrated and the residue was purified by silica gel column chromatography with pure $CH_2Cl_2$ to give compound 6 as white solid (230 mg, 92% yield). $^1H$ NMR (400 MHz, $CDCl_3$, 25° C.): δ=3.18-3.22 (m, 2H), 3.81 (s, 3H), 4.44-4.49 (m, 1H), 4.79-4.81 (m, 1H), 5.20-5.21 (m, 1H), 6.62-6.63 (m, 1H), 6.84-6.86 (m, 4H), 7.23-7.46 (m, 9H,), 7.85 (d, J=7.6 Hz, 1H); $^{13}C$ NMR (100 MHz, $CDCl_3$, 25° C.): δ=55.2, 63.7, 76.2, 86.0, 88.3, 103.3, 113.1, 126.8, 127.8, 128.1, 130.1, 136.0, 144.8, 150.3, 158.5; HRMS: m/z: calcd for $C_{26}H_{25}O_5$: 417.1702. found: 417.1708 [M-H]$^-$.

2,2'-Anhydro-1-[2'-deoxy-3'-acetyl-5'-O-(4,4-dimethoxytrityl)-β-D-arabino furanosyl]-uracil (7) in FIG. 9

To a solution of 3a (320 mg, 0.6 mmol) in THF, acetic anhydride (0.19 mL, 2 mmol) was added, followed by several drops of triethylamine. The mixture was stirred at 50 degree for further 45 minutes (monitored by TLC, 5% MeOH in $CH_2Cl_2$) before quenched by methanol (4 mL). The solvent were removed under reduced pressure and the residue was re-dissolved in $CH_2Cl_2$ (40 mL). The suspension was washed with sodium bicarbonate (sat., 2×15 mL) and sat. brine (2×15 mL). The organic layer was dried over $MgSO_4$ (s), concentrated under reduced pressure, and the resulting residue was subjected to silica gel chromatography (0-5% MeOH in $CH_2Cl_2$) to give 7 (291 mg, 85% yield) as white solids. 7: $^1H$ NMR (400 MHz, $CDCl_3$, 25° C.): δ=2.14 (s, 3H), 2.99-3.06 (m, 2H), 3.81 (s, 6H), 4.45 (m, 1H), 5.30-5.32 (m, 1H), 5.40 (m, 1H), 5.86 (d, J=7.6 Hz, 1H), 6.27 (d, J=5.6 Hz, 1H), 6.80-6.83 (m, 4H), 7.21-7.35 (m, 10H); $^{13}C$ NMR (100 MHz, $CDCl_3$, 25° C.): δ=20.7, 55.3, 62.6, 77.0, 85.8, 86.3, 86.6, 90.4, 110.2, 113.3, 127.1, 128.0, 129.8, 135.2, 144.1, 158.6, 134.5, 159.1, 169.4, 171.2; HRMS: m/z: calcd for $C_{32}H_{31}N_2O_8$: 571.2080. found 571.2080 [M+H]$^+$.

5'-O-(4,4-dimethoxytrityl)-2',3'-didehydro-2',3'-dideoxyuridine (8) in FIG. 9

To a stirred suspension of $NaBH_4$ (12 mg, 0.3 mmol) in anhydrous THF (5 mL), under argon, dimethyl ditelluride (0.05 mL, 0.3 mmol) was added, followed by several drops of dry ethanol until bubbles were formed. The suspension was heated to 50° C., and the THF solution of the starting material 7, (170 mg, 3 mmol) was added. The reaction completed in 3 hours, which monitored by TLC. Then the solvents were evaporated and the residue was dissolved in $CH_2Cl_2$ and washed with water. The organic solution was dried over $MgSO_4$ and concentrated. The crude product was purified by silica gel column chromatography with 0-3% methanol in $CH_2Cl_2$ to give 90% yields of 8. $^1H$ NMR (400 MHz, $CDCl_3$, 25° C.): δ=3.47-3.48 (m, 2H), 3.82 (s, 3H), 4.97-4.98 (m, 1H), 5.06 (d, 1H, J=7.6 Hz), 5.89-5.91 (m, 1H), 6.35-6.37 (m, 1H), 6.84-6.86 (m, 4H), 7.05 (d, J=2.0 Hz, 1H), 7.27-7.38 (m, 9H), 7.85 (d, J=7.6 Hz, 1H); $^{13}C$ NMR (100 MHz, $CDCl_3$, 25° C.): δ=55.4, 64.2, 86.1, 86.9, 89.6, 102.2, 113.2, 127.1, 127.8, 127.4, 129.1, 130.20, 150.6, 127.1, 134.6, 141.4, 150.6, 158.6, 163.2; HRMS: m/z: calcd for $C_{30}H_{27}N_2O_6$: 511.1869, found 511.1868 [M–H]$^-$.

2'-deoxy-2'-methyltellanyl-5'-O-(4,4'-dimethoxytrityl)-uridine (9a) and 2'-deoxy-2'-methyltellanyl-5'-O-(4,4'-dimethoxytrityl)-5-methyluridine (9b) in FIG. 10

To a THF solution of dimethyl ditelluride ($CH_3TeTeCH_3$, 0.2 ml, 1.1 mmol, in 10 mL of THF) located in an ice bath under argon, was added 1M THF solution of $LiAlH_4$ (0.55 mmol) in 5 min. After the solution turned to slightly yellow, 12-crown-4 (0.6 mmol, 0.1 mL) was added and the mixture was stirred at 0° C. for further 20 min before the starting material 3a and 3b (0.57 g and 0.58 g respectively in THF, 1.0 mmol) was added dropwise. The reaction was monitored by TLC (5% $CH_3OH$ in $CH_2Cl_2$) and it was found that the yield reached maximum in 4-5 hours before it dropped again by the generation of compound 6. The reaction was quenched by adding 10 mL of saturated sodium chloride, followed by adding 10 mL of $CH_2Cl_2$, the organic solvent was further washed, dried over anhydrous $MgSO_4$ and removed under reduced pressure. The residue was then purified by a silica gel column (equilibrated with $CH_2Cl_2$) eluted with a methanol/methylene chloride gradient ($CH_3OH$ in $CH_2Cl_2$, 0-3%) to afford the pure foamy product 9a and 9b in 40%-47% yield. 9a: $^1H$ NMR (400 MHz, $CDCl_3$, 25° C.): δ=2.0 (s, 3H), 2.5 (s, 1H), 3.52 (dd, J1=2.8 Hz, J2=7.2 Hz, 2H), 3.69 (t, J=4 Hz, 1H), 3.82 (s, 6H), 4.21-4.23 (m, 1H), 4.31-4.36 (m, 1H), 5.40 (d, J=8.4 Hz, 1H), 6.33 (d, J=8.4 Hz, 1H), 6.86-6.88 (m, 4H), 7.26-7.39 (m, 9H), 7.77 (d, J=8.4 Hz, 1H), 8.38 (br, 1H); $^{13}$C NMR (100 MHz, CDCl$_3$, 25° C.): δ=−21.2, 33.35, 55.29, 63.37, 73.75, 84.51, 87.29, 89.90, 102.73, 113.35, 127.28, 128.07, 130.08, 135.12, 139.77, 144.20, 150.23, 158.79, 162.64; HRMS: m/z: calcd for C$_{31}$H$_{31}$N$_2$O$_7$Te: 673.1194. found: 673.1204 [M−H]$^−$. 9b: $^1$H NMR (400 MHz, CDCl$_3$, 25° C.): δ=1.43 (s, 3H), 1.99 (s, 3H), 3.47 (dd, J1=1.6 Hz, J2=9.6 Hz, 2H), 3.70-3.74 (m, 1H), 3.82 (s, 6H), 4.24-4.25 (m, 1H), 4.36-4.37 (m, 1H), 6.37 (d, J=9.2 Hz, 1H), 6.85-6.87 (m, 4H), 7.26-7.40 (m, 9H), 7.60 (s, 1H), 8.03 (br, 1H); $^{13}$C NMR (100 MHz, CDCl$_3$, 25° C.): δ=−20.8, 11.71, 33.11, 55.29, 63.86, 74.62, 84.64, 87.19, 89.90, 111.75, 113.32, 127.29, 128.09, 129.14, 135.20, 135.16, 144.21, 150.48, 158.82, 163.41; HRMS: m/z: calcd for C$_{32}$H$_{33}$N$_2$O$_7$Te: 687.1350. found: 687.1354 [M−H$^+$]$^−$.

2'-methyltellanyl-5'-O-(4,4'-dimethoxytriphenylmethyl)-uridine 3'-O-(2-cyanoethyl)diisopropylamino phosphoramidite (10a) and 2'-methyltellanyl-5'-O-(4,4'-dimethoxytriphenylmethyl)-5-methyluridine-3'-O-(2-cyanoethyl)diisopropylamino phosphoramidite (10b) in FIG. 10

To the flask (25 mL) containing 9a or 9b (230 mg and 234 mg separately, 0.34 mmol) under argon, dry methylene chloride (2.5 mL), N,N-diisopropylethylamine (0.1 mL, 0.51 mmol, 1.5 eq.), and 2-cyanoethyl N,N-diisopropyl-chlorophosphoramidite (120 mg, 0.51 mmol, 1.5 eq.) were added sequentially. The reaction mixture was stirred at −10° C. in an ice-salt bath under argon for 10 minutes, followed by removal of the bath. The reaction was completed in 45 minutes at room temperature (indicated by TLC, 5% MeOH in CH$_2$Cl$_2$), generating a mixture of two diastereomers. The reaction was then quenched with NaHCO$_3$ (2 mL, sat.), stirred for 5 min, and the product was then extracted with CH$_2$Cl$_2$ (3×5 mL). The combined organic layer was washed with NaCl (10 mL, sat.) and dried over MgSO$_4$ (s) for 20 min, followed by filtration. The solvent was then evaporated under reduced pressure and the crude product was re-dissolved in CH$_2$Cl$_2$ (2 mL). This solution was added drop-wise to petroleum ether (200 mL) under vigorous stirring, generating white precipitate. The petroleum ether solution was decanted. The crude product was re-dissolved again in CH$_2$Cl$_2$ (2 mL) and then loaded into an Al$_2$O$_3$ column (neutral) that was equilibrated with CH$_2$Cl$_2$/Hexanes (1:1). The column was eluded with a gradient of methylene chloride and ethyl acetate [CH$_2$Cl$_2$ to CH$_2$Cl$_2$/EtOAc (7:3)]. After solvent evaporation and dry over high vacuum, the white 10a and 10b was obtained as a white foamy product (88-90% yield). 10a: $^1$H NMR (400 MHz, CDCl$_3$, 25° C.): δ=0.85-1.38 (m, 24H), 1.98 and 1.99 (2x s, 6H), 2.41 and 2.67 (2x t, J=7.6 Hz, 4H), 3.42-3.69 (m, 12H), 3.83 (s, 12H), 3.89-4.05 (m, 4H), 4.22 and 4.30 (2x m, 2H), 4.57-4.77 (m, 2H), 6.43 and 6.55 (2x d, J=8.6 Hz, 2H), 6.80-6.92 (m, 8H), 7.16-7.45 (m, 18), 7.78 and 7.79 (s, 2H); $^{13}$C NMR (CDCl$_3$, 25° C.): δ=−21.32, 19.16, 19.66, 20.88, 24.81, 24.44, 43.30, 43.46, 46.34, 47.53, 51.47 and 51.85, 55.62, 57.03, 58.39, 62.52, 73.36, 73.67, 84.57, 87.35, 88.12, 103.39, 113.42, 117.28, 127.21, 127.94, 128.36, 130.19, 130.25, 135.17, 135.38, 139.53, 144.20, 150.42, 158.80, 163.19. $^{31}$P NMR (160 MHz, CDCl$_3$, 25° C.): δ=148.5, 149.2; ESI-TOF: m/z calcd for C$_{40}$H$_{48}$N$_4$O$_8$PTe: 873.2272. found 873.2264. 10b: $^1$H NMR (400 MHz, CDCl$_3$, 25° C.): δ=0.89-1.42 (m, 24H), 1.40 (2x s, 6H), 2.10 (2x s, 6H), 2.42 and 2.69 (2x t, J=7.8 Hz, 4H), 3.48-3.72 (m, 12H), 3.82 (s, 12H), 3.90-4.05 (m, 2H), 4.22 and 4.31 (2x m, 2H), 4.58-4.72 (m, 2H), 6.42 (d, J=8.6 Hz, 2H), 6.79-6.92 (m, 8H), 7.20-7.45 (m, 18H), 7.62 (2x s, 2H), 8.25 (br, 2H); $^{13}$C NMR (100 MHz, CDCl$_3$, 25° C.): δ=−21.32, 4.58, 4.72, 20.13, 20.16, 20.48, 20.55, 22.52, 24.39, 24.47, 24.59, 24.68, 24.76, 24.83, 43.21, 43.32, 43.34, 43.41, 46.35, 46.42, 47.37, 47.42, 50.36, 55.32, 63.29, 63.33, 74.90, 75.09, 84.99, 87.28, 89.36, 111.70, 113.44, 117.29, 126.99, 127.83, 128.55, 130.20, 130.41, 135.23, 135.41, 135.44, 144.11, 150.38, 158.86, 163.35. $^{31}$P NMR (160 MHz, CDCl$_3$, 25° C.): δ=148.6, 149.5; ESI-TOF: m/z calcd for C$_{41}$H$_{52}$N$_4$O$_8$PTe: 889.2585. found 889.2587.

Synthesis of the Te-Derivatized Nucleic Acids (TeNA):

All DNA and RNA oligonucleotides were synthesized chemically on a 1.0 umol scale using an ABI3400 DNA/RNA Synthesizer. The concentration of the Te modified phosphoramidites was less than conventional ones (0.06 M in stead of 0.1M). Coupling was carried out using a 5-(benzylmercapto)-1H-tetrazole (5-BMT) in acetonitrile (0.25 M) as activator. All the other native phosphoramidites were protected with ultra-mild deprotection on the nucleobases. The coupling time for the Te phosphoramidite was set to 60 seconds. All the oligonucleotides were prepared with DMTr-on mode. After synthesis, the beads were treated with 1 mL of K$_2$CO$_3$ (0.05M) for 8 h, then the supernant was neutralized with 1M HCl solution and treated with 5 uL of 1M borane in THF before HPLC analysis and purification. The 5'-DMTr deprotection of DNAs was performed in a 3% trichloroacetic acid solution for 3 min, followed by and petroleum ether extraction to remove DMTr-OH.

HPLC Analysis and Purification:

The DNA oligonucleotides were analyzed and purified by reverse phase high performance liquid chromatography (RP-HPLC) in both DMTr-on and DMTr-off mode. Purification was carried out using a 21.2×250 mm Zorbax, RX-C18 column at a flow rate of 6 mL/min. Buffer A consisted of 20 mM triethylammonium acetate (TEAAc, pH 7.1), while buffer B contained 50% aqueous acetonitrile in buffer A. Similarly, analysis was performed on a Zorbax SB-C18 column (4.6× 250 mm) at a flow of 1.0 mL/min using the same buffer system. The DMTr-on oligonucleotides were eluded with up to 100% buffer B in 20 min in a linear gradient, while the DMTr-off oligonucleotides were eluted with up to 70% of buffer B in a linear gradient in the same period of time. The collected fractions were lyophilized and re-dissolved in small amount of water. It's better to adjust the pH to 7.0 after the final purification.

C. Thermo-Denaturation of Duplex DNAs

Figure 6:
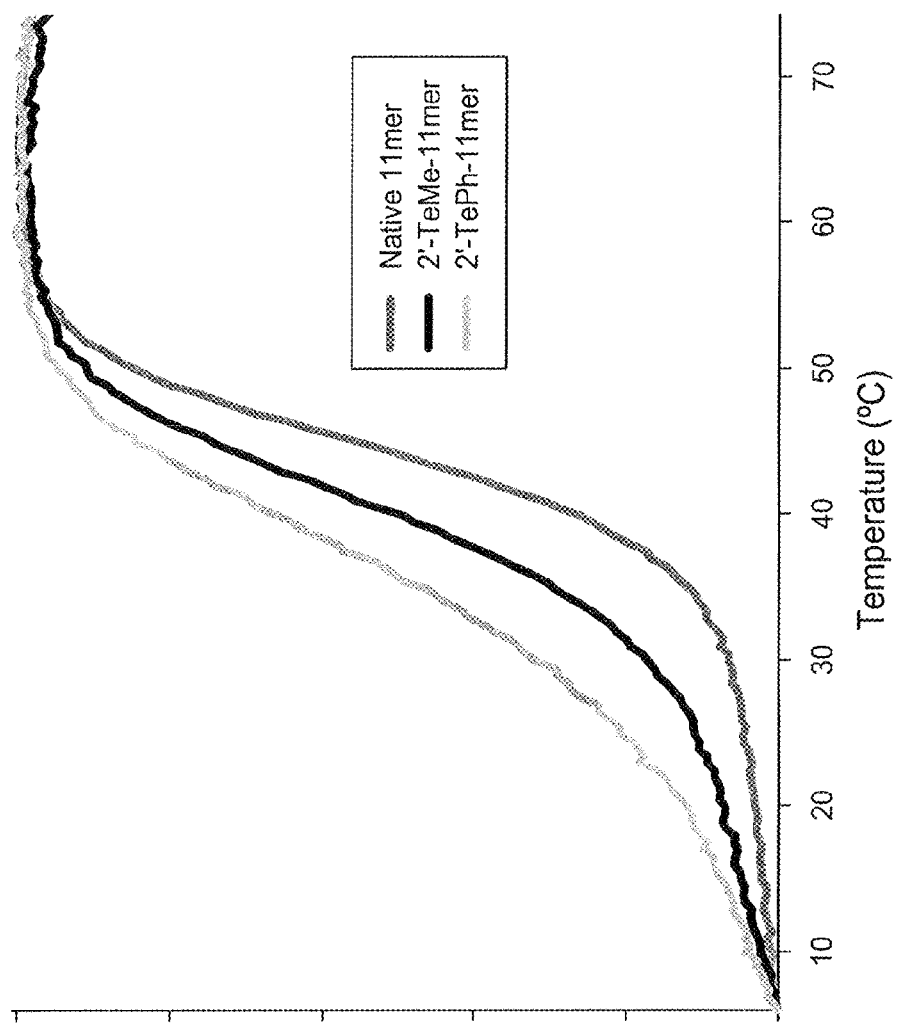
FIG. 6. A representation of the normalized thermo-denaturation curves of the DNA duplexes [5'-C(2'-TeX-dU)TCT-TGTCCG-3'&3'-CGGACAAGAAG-5', X=native, Me or Ph].
Figure 7:
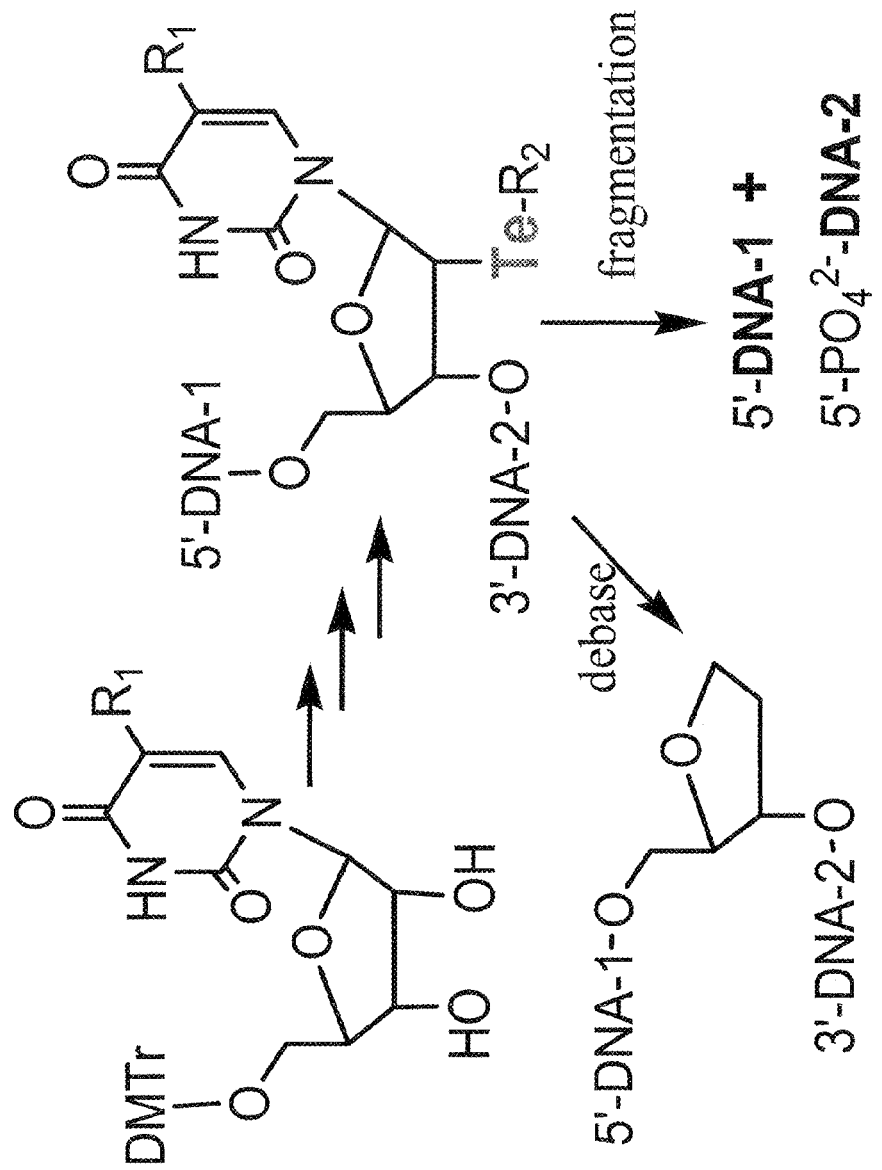
FIG. 7. A representation of a simplified flowchart of the 2'-Te-oligonucleotide synthesis according to some forms of the disclosure.

Solution of the duplex DNA (2 uM) was prepared by dissolving the DNAs in a buffer containing 50 mM NaCl, 10 mM NaH$_2$PO$_4$—Na$_2$HPO$_4$ (pH 6.5), 0.1 mM EDTA and 10 mM MgCl$_2$. The solution was heated to 70° C. for 2 min and cooled slowly to room temperature, followed by storing at 4° C. for overnight before measurement. The Tm curves were acquired at 260 nm by heating the samples from 5 to 70° C. at a rate of 0.5° C./min using Cary 300 UV-Visible Spectrophotometer with a temperature controller. FIG. 6 shows the normalized thermo-denaturation curves of the DNA duplexes [5'-C(2'-TeX-dU)TCTTGTCCG-3'&3'-CGGACAAGAAG-5', X=native, Me, or Ph]. The samples (1 mM duplex) were heated from 6 to 75° C. with a rate of 0.5° C./min. The red, blue and green curves represent the native, 2'-TeMe and 2'-TePh duplex, respectively, and are labelled in FIG. 6. The average Tm (four measurements) for each duplex is: 44.0±0.1° C. (native), 40.7±0.1° C. (2'-TeMe) and 36.8±0.2° C. (2'-TePh). Figure S-2 shows the thermal denaturation curves of 2'-TeX modified self-complementary sequence 5'-GU(2'-TePh)GTACAC-3' (X=Me or Ph). The samples (1 mM duplex) were heated from 6 to 70° C. with a rate of 0.5°

C./min. The circle (red), diamond (blue) and hexagon (purple) curves represent the native, 2'-TeMe and 2'-TePh DNA duplexes, respectively, with the averaged Tm (four times): 39.4° C. (native), 28.6° C. (2'-TeMe) and 23.4° C. (2'-TePh).

Discussion and Summary

Figure 13:
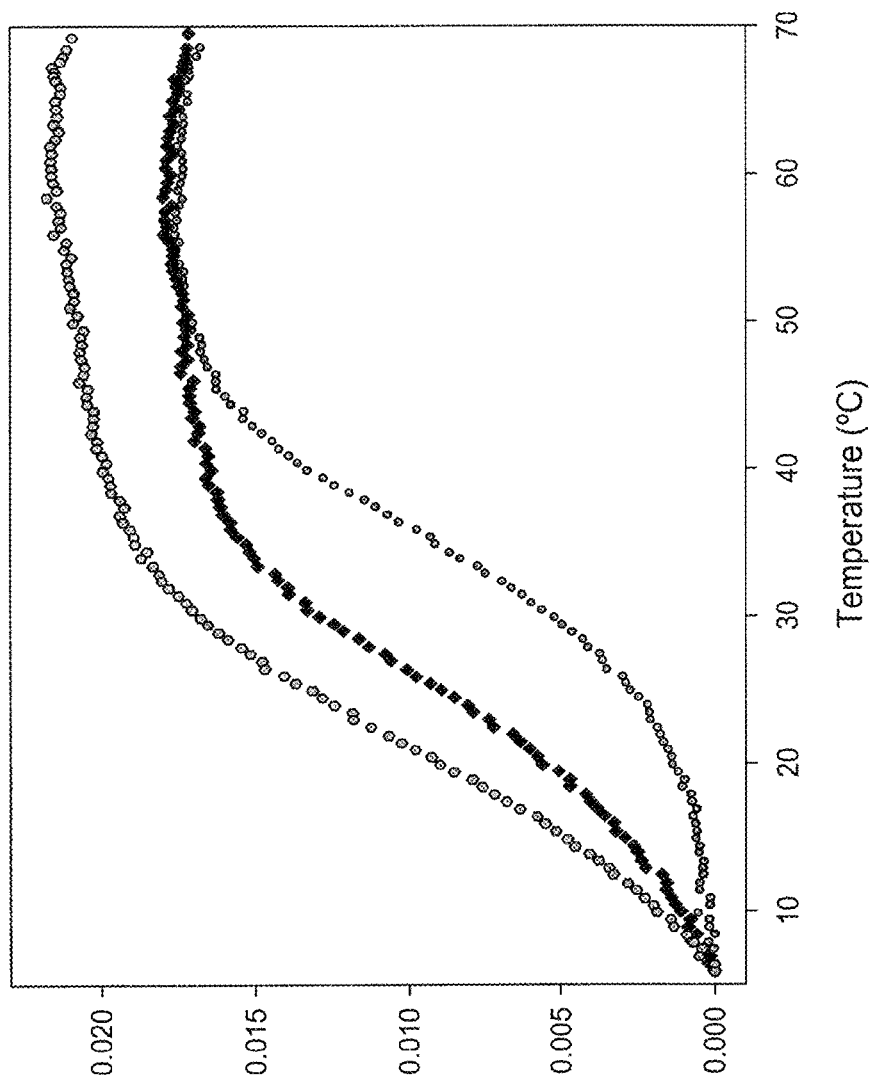
FIG. 13. A representation of the thermal denaturation curves of 2'-TeX modified self-complementary sequence 5'-G U(2'-TePh)GTACAC-3' (X=native, Me, or Ph).

Due to the size of Te atom, It is anticipated that the incorporated Te-functionalities at the 2' position perturb the DNA duplexes. In addition, It is expected that the 2'-Te-Ph moiety causes more perturbation than the 2'-Te-Me. Later, the Te-modified duplex stability was investigated by measuring their UV-melting temperatures. In the case of a self-complementary duplex [5'-G(2'-TeX-dU)GTACAC-3', X=Ph or Me]$_2$, where double Te-modifications were introduced to this short DNA duplex, the melting temperatures dropped dramatically (FIG. 13). In the case of the 2'-TePh-DNA duplex, the Tm decreased by 15° C. (7.5° C. per modification) while the 2'-TeMe-DNA duplex by 10° C. (5.0° C. per modification) compared with the native duplex. It suggests that short duplex of the self-complimentary DNA can not accommodate these two bulky modifications well. When introducing the Te-functionalities to a non-self-complementary duplex [5'-C(2'-TeX-dU)TCTTGTCCG-3' and 5'-CGGACAAGA-AG-3', X=Me or Ph], it was observed that the melting temperatures of the native, 2'-TeMe and 2'-TePh duplexes were 44.0, 40.7 and 36.8° C., respectively. The difference between the native and 2'-Te-Me modified DNAs are 3.3° C. It is noteworthy that when the TeMe moiety is introduced close to a terminal position, the Te-modification is relatively well accommodated (FIG. 6). Since the termini are usually dynamic and spacious, the result suggests that the dynamics and available space allow a better accommodation. Therefore, the perturbation caused by the 2'-Te-functionality is most likely a local event, and this bulky Te-modification may be useful in investigating the formation of DNA or RNA loop, bulge, and other secondary or 3D structures.

In summary, disclosed is the synthesis of the Te-derivatized nucleoside phosphoramidites and Te-oligonucleotides with a high coupling yield. Several 2'-Te-modified oligonucleotides were synthesized and characterized by HPLC and MS. The disclosure demonstrated that both of the 2'-TeMe and 2'-TePh functionalities are compatible with the solid-phase synthesis, deprotection and purification. In addition, The disclosure revealed the redox property of the Te-functionalities and the interchange of the telluride and telluroxide DNAs by redox reactions. The disclosure also found that the 2'-Te-Ph DNA can be reductively or oxidatively cleaved, while the nucleobase of the 2'-Te-Me DNA can be eliminated via the 1',2' elimination, creating an abasic site. This Te-DNA system may be useful in studying the DNA fragmentation and nucleobase damage [M. J. Maul, T. R. M. Barends, A. F. Glas, M. J. Cryle, T. Domratcheva, S. Schneider, I. Schlichting, T. Carell, Angew. Chem. Int. Ed. 2008, 47, 10076-10080]. Furthermore, in the UV-melting study of the 2'-Te-modified DNA duplexes, as expected, it was observed the Tm decreases of the Te-DNA duplexes. Since the Tm decreases are dependent on the location of the Te-modifications and the size of the protecting groups, the Te-derivatization may be a useful strategy in probing DNA and RNA polymerization and catalysis [M. Rothlingshofer, E. Kervio, T. Lommel, U. Plutowski, A. Hochgesand, C. Richert, Angew. Chem. Int. Ed. Engl. 2008, 47, 6065-6068; M. Renders, M. Abramov, M. Froeyen, P. Herdewijn, Chem. Eur. J. 2009, 15, articles online in advance of print; H. Xiao, H. Murakami, H. Suga, A. R. Ferre-D'Amare, Nature 2008, 454, 358-361.]. Moreover, this Te-derivatization of nucleic acids has great potentials in nucleic acid X-ray crystallography as well as in structural and functional studies of nucleic acid-protein complexes.

References

W. A. Hendrickson, J. R. Horton, D. M. LeMaster, EMBO. J. 1990, 9, 1665-1672.

W. A. Hendrickson, Science 1991, 254, 51-58.

W. A. Hendrickson, Trends. Biochem. Sci., 2001, 25, 637-643.

J. Sheng, Z. Huang, Inter. J. Mol. Sci, 2008, 9, 258-271.

J. C. Williams, Z. Huang, Chem. Biodiversity, 2008, 5, 396-407.

N. Carrasco, D. Ginsburg, Q. Du, Z. Huang, Nucleosides, Nucleotides, Nucleic Acids 2001, 20, 1723-1734.

Q. Du, N. Carrasco, M. Teplova, C. J. Wilds, M. Egli, Z. Huang, J. Am. Chem. Soc. 2002, 124, 24-25.

N. Carrasco, Y. Buzin, E. Tyson, E. Halpert, Z. Huang, Nucleic Acids Res. 2004, 32, 1638-1646.

J. Jiang, J. Sheng, N. Carrasco, Z. Huang, Nucleic Acids Res. 2007, 35, 477-485.

J. Sheng, J. Jiang, J. Salon, Z. Huang, Org. Lett. 2007, 9, 749-752.

C. Hobartner, R. Micura, J. Am. Chem. Soc. 2004, 126, 1141-1149.

H. Moroder, C. Kreutz, K. Lang, A. Serganov, R. Micura, J. Am. Chem. Soc. 2006, 128, 9909-9918.

L. S. Jeong, D. K. Tosh, H. O. Kim, T. Wang, X. Hou, H. S. Yun, Y. Kwon, S. K. Lee, J. Choi, L. X. Zhao, Org. Lett. 2008, 10, 209-212.

J. K. Watts, B. D. Johnston, K. Jayakanthan, A. S. Wahba, B. M. Pinto, M. J. Damha, J. Am. Chem. Soc. 2008, 130, 8578-8579.

C. J. Wilds, R. Pattanayek, C. Pan, Z. Wawrzak, M. Egli, J. Am. Chem. Soc. 2002, 124, 14910-14916.

N. Carrasco, J. Caton-Williams, G. Brandt, S. Wang, Z. Huang, Angew. Chem. Int. Ed. Engl. 2006, 45, 94-97.

G. Brandt, N. Carrasco, Z. Huang, Biochemistry 2006, 45, 8972-8977.

J. Salon, J. Sheng, J. Jiang, G. Chen, J. Caton-Williams, Z. Huang, J. Am. Chem. Soc. 2007, 129, 4862-4863.

J. Caton-Williams, Z. Huang, Angew. Chem. Int. Ed. Engl. 2008, 47, 1723-1725.

J. Salon, J. Jiang, J. Sheng, O. O. Gerlits, Z. Huang, Nucleic Acids Res. 2008, 36, 7009-7018.

L. Moroder, J. Pept. Sci. 2005, 11, 187-214.

S. E. Ramadan, A. A. Razak, A. M. Ragab, M. el-Meleigy, Biol. Trace Elem. Res. 1989, 20, 225-232.

J. O. Boles, K. Lewinski, M. Kunkle, J. D. Odom, B. Dunlap, L. Lebioda, M. Hatada, Nat. Struct. Biol. 1994, 1, 283-284.

N. Budisa, W. Karnbrock, S. Steinbacher, A. Humm, L. Prade, T. Neuefeind, L. Moroder, R. Huber, J. Mol. Biol. 1997, 270, 616-623.

N. Budisa, B. Steipe, P. Demange, C. Eckerskorn, J. Kellermann, R. Huber, Eur. J. Biochem. 1995, 230, 788-796.

M. Farina, F. A. Soares, G. Zeni, D. O. Souza, J. B. Rocha, Toxicol. Lett. 2004, 146, 227-235.

W. Karnbrock, E. Weyher, N. Budisa, R. Huber, L. Moroder, J. Am. Chem. Soc. 1996, 118, 913-914.

C. W. Nogueira, G. Zeni, J. B. Rocha, Chem. Rev. 2004, 104, 6255-6285.

J. Sheng, A. E. Hassan, Z. Huang, J. Org. Chem. 2008, 73, 3725-3729.

J. Chen, J. Stubbe, Biochem. 2004, 43, 5278-5286.

K. Usui, M. Aso, M. Fukuda, H. Suemune, J. Org. Chem. 2008, 73, 241-248.

M. J. Maul, T. R. M. Barends, A. F. Glas, M. J. Cryle, T. Domratcheva, S. Schneider, I. Schlichting, T. Carell, Angew. Chem. Int. Ed. 2008, 47, 10076-10080.

M. Rothlingshofer, E. Kervio, T. Lommel, U. Plutowski, A. Hochgesand, C. Richert, *Angew. Chem. Int. Ed. Engl.* 2008, 47, 6065-6068.

M. Renders, M. Abramov, M. Froeyen, P. Herdewijn, *Chem. Eur. J.* 2009, 15, articles online in advance of print.

H. Xiao, H. Murakami, H. Suga, A. R. Ferre-D'Amare, *Nature* 2008, 454, 358-361.

What is claimed is:

1. A compound of formula (I), or a tautomer thereof, or a derivative thereof, or a pharmaceutically acceptable salt of said compound or said tautomer or said derivative;

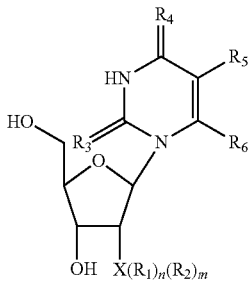

wherein:

X is tellurium;

$R_1$ is linear or branched alkyl, or aryl;

$R_2$ is selected from the group consisting of hydrogen, halogen, alkyl, aryl, hydroxyl, thiol, amino, alkyloxyl, aryloxyl, acyloxyl, alkylthiol, arylthiol, alkylseleno, arylseleno, alkyltelluro, aryltelluro, alkylamino, arylamino and acylamino;

$R_3$ is selected from the group consisting of oxygen, sulfur, selenium, tellurium, amino, alkylamino, arylamino and acylamino;

$R_4$ is selected from the group consisting of hydrogen, halogen, alkyl, aryl, hydroxyl, thiol, alkylthiol, arylthiol, oxygen, sulfur, selenium, tellurium, amino, alkylamino, arylamino and acylamino;

$R_5$ and $R_6$ are each independently selected from the group consisting of hydrogen, halogen, alkyl, aryl, hydroxyl, thiol, amino, alkyloxyl, aryloxyl, acyloxyl, alkylthiol, arylthiol, alkylamino, arylamino and acylamino; and n and m are a subscript selected from 0 to 20.

2. The compound according to claim 1, wherein said tautomer is a compound of formula (II):

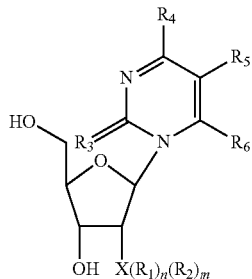

wherein R4 is selected from the group consisting of hydrogen, halogen, alkyl, aryl, hydroxyl, thiol, alkylthiol, arylthiol, amino, alkylamino, arylamino and acylamino.

3. The compound according to claim 1 wherein the unsaturated six-member base ring of the nucleobase is cytosine, thymine or uracil; and wherein X is tellurium, and $R_1$ is linear or branched alkyl, or aryl; or wherein $R_5$ is hydrogen or alkyl.

4. The compound of claim 1, wherein the compound is compatible with solid-phase synthesis.

5. The compound of claim 1, wherein the compound may be reductively or oxidatively cleaved to create an abasic site.

6. The compound of claim 1, wherein an elimination reaction may be used to create an abasic site.

7. The compound of claim 1 for use in probing DNA and RNA polymerization and catalysis.

8. The compound of claim 1 for use in nucleic acid X-ray crystallography.

9. The compound of claim 1 for use in structural and functional studies of nucleic acid protein complexes.

10. A derivative of the compound of claim 1, wherein said derivative is a compound of formula (III):

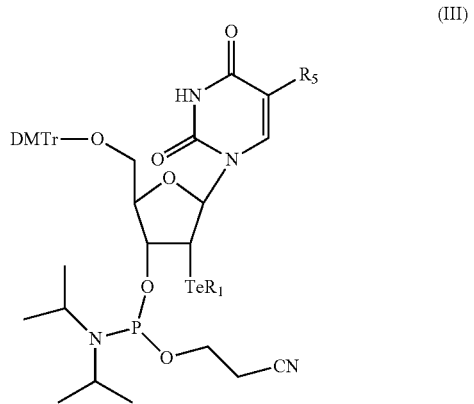

and wherein DMTr represents dimethoxytrityl.

11. The derivative of claim 10, wherein said $R_1$ is methyl or phenyl; or wherein said $R_5$ is hydrogen or methyl.

12. A derivative of the compound of claim 1, wherein said derivative is a compound of formula (IV):

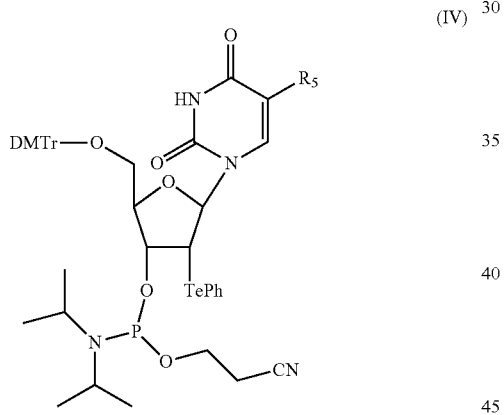

and wherein $R_5$ is hydrogen or methyl.

13. A derivative of the compound of claim 1, wherein said derivative is compound of formula (V):

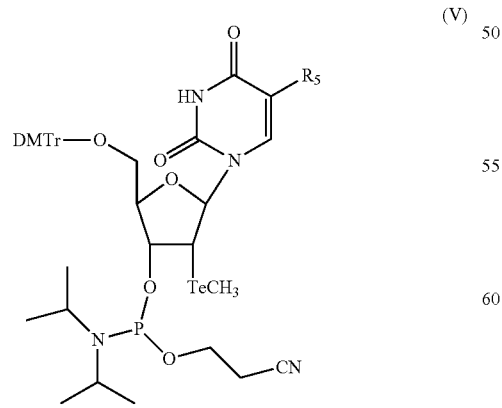

and wherein $R_5$ is hydrogen or methyl.

14. A derivative of the compound of claim 1, wherein said derivative is an telluride(Te)-oligonucleotide, telluride(Te)-DNA, or telluride(Te)-RNA.

15. The derivative of claim 14, wherein said telluride DNA (or RNA) has a structure of formula (VI):

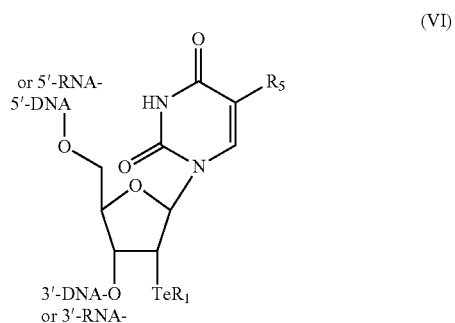

and wherein $R_1$ is methyl or phenyl; and $R_5$ is hydrogen or methyl.

16. The derivative of claim 14, wherein said telluride DNA (or RNA) is oxidized to form a telluroxide DNA (or RNA) and/or tellurone DNA (or RNA) which has a structure of formula VIIa or VIIb respectively:

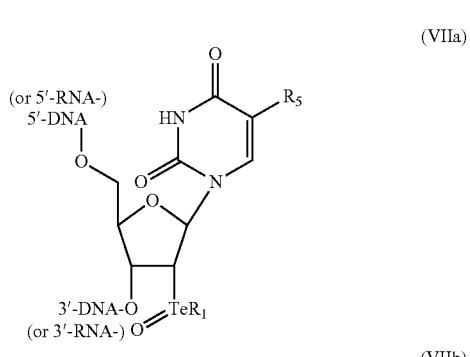

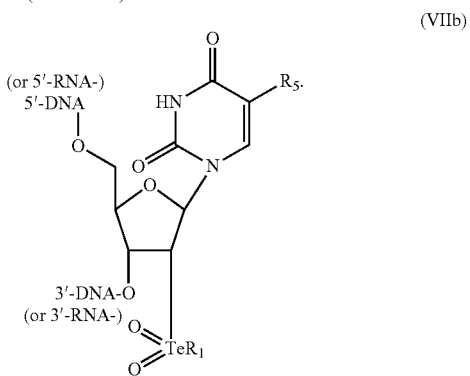

17. A derivative of the compound of claim 1, wherein said derivative is used as a building block to construct the corresponding telluride(Te)-oligonucleotide, telluride(Te)-DNA, or telluride(Te)-RNA.

* * * * *